US010045937B2

(12) United States Patent
von Recum et al.

(10) Patent No.: US 10,045,937 B2
(45) Date of Patent: *Aug. 14, 2018

(54) THERAPEUTIC AGENT DELIVERY SYSTEM AND METHOD

(75) Inventors: Horst A. von Recum, Cleveland Heights, OH (US); Julius N. Korley, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/376,298

(22) PCT Filed: Jun. 3, 2010

(86) PCT No.: PCT/US2010/037183
§ 371 (c)(1),
(2), (4) Date: May 21, 2012

(87) PCT Pub. No.: WO2010/141667
PCT Pub. Date: Dec. 9, 2010

(65) Prior Publication Data
US 2012/0220518 A1 Aug. 30, 2012

Related U.S. Application Data

(60) Provisional application No. 61/183,698, filed on Jun. 3, 2009.

(51) Int. Cl.
| | | |
|---|---|---|
| *A61K 47/26* | (2006.01) | |
| *A61K 9/00* | (2006.01) | |
| *A61K 9/06* | (2006.01) | |
| *A61K 47/40* | (2006.01) | |
| *A61K 47/48* | (2006.01) | |
| *B82Y 5/00* | (2011.01) | |
| *C08B 37/16* | (2006.01) | |
| *C08L 5/16* | (2006.01) | |

(52) U.S. Cl.
CPC .............. *A61K 9/0024* (2013.01); *A61K 9/06* (2013.01); *A61K 47/40* (2013.01); *A61K 47/48176* (2013.01); *A61K 47/48192* (2013.01); *A61K 47/48215* (2013.01); *A61K 47/48969* (2013.01); *B82Y 5/00* (2013.01); *C08B 37/0012* (2013.01); *C08B 37/0015* (2013.01); *C08L 5/16* (2013.01)

(58) Field of Classification Search
CPC .... C08L 75/04; C08L 2666/04; C08L 101/02; C08L 51/0003; C08L 75/00; C08L 83/10; G03F 7/033; G03F 7/038; G03F 7/26; A61L 27/18; A61L 24/04; A61L 24/08; A61L 27/56; A61K 31/74; A61K 31/785; A61K 51/08; A61K 2300/00; A61K 45/06; A61K 47/48969; A61K 47/40; A61K 31/724; A61K 9/0051; A61K 31/00; C12N 2310/3513; C08B 37/0012; C08B 37/0015

See application file for complete search history.

(56) References Cited

U.S. PATENT DOCUMENTS

| | | | | |
|---|---|---|---|---|
| 6,678,553 | B2 * | 1/2004 | Lerner et al. | 604/20 |
| 7,141,540 | B2 * | 11/2006 | Wang et al. | 514/1 |
| 9,642,920 | B2 * | 5/2017 | von Recum | C08B 37/0015 |
| 2004/0043052 | A1 * | 3/2004 | Hunter | A61L 27/34 424/426 |
| 2004/0109888 | A1 * | 6/2004 | Pun et al. | 424/450 |
| 2005/0276814 | A1 | 12/2005 | Gilbert et al. | |
| 2005/0276841 | A1 * | 12/2005 | Davis et al. | 424/443 |
| 2006/0147492 | A1 * | 7/2006 | Hunter | A61B 17/11 424/426 |
| 2006/0177483 | A1 | 8/2006 | Byrne et al. | |
| 2007/0026069 | A1 | 2/2007 | Shastri et al. | |
| 2007/0135605 | A1 * | 6/2007 | Hadba | C08G 18/3278 528/44 |
| 2008/0206146 | A1 | 8/2008 | Akhtari et al. | |
| 2008/0254094 | A1 | 10/2008 | Martel et al. | |
| 2009/0176737 | A1 | 7/2009 | Tabuchi et al. | |
| 2015/0010608 | A1 | 1/2015 | von Recum et al. | |

FOREIGN PATENT DOCUMENTS

| | | | | |
|---|---|---|---|---|
| WO | WO 2007/067806 A2 * | 6/2007 | | C08G 18/00 |
| WO | WO-2007/077783 A1 | 7/2007 | | |

OTHER PUBLICATIONS

Daoud-Mahammed et al. Self-assembling cyclodextrin based hydrogels for the sustained delivery of hydrophobic drugs. J Biomed Mater Res A. Sep. 2008;86(3):736-48.*
Davis et al. Cyclodextrin-based pharmaceutics: past, present and future. Nat Rev Drug Discov. Dec. 2004;3(12):1023-35.*
Hildebrand et al. Surface coatings for biological activation and functionalization of medical devices. Surface & Coatings Technology 200. 2006: 6318-6324.*
Cavalli et al. Cyclodextrin-based Nanosponges for Drug Delivery. Journal of Inclusion Phenomena and Macrocyclic Chemistry (2006) 56: 209-213.*
Mura et al. Characterization of physicochemical properties of naproxen systems with amorphous beta-cyclodextrin-epichlorohydrin polymers. J Pharm Biomed Anal. Aug. 1, 2002;29(6):1015-24.*

(Continued)

*Primary Examiner* — Marcela M Cordero Garcia
*Assistant Examiner* — Jia-Hai Lee
(74) *Attorney, Agent, or Firm* — Tarolli, Sundheim, Covell & Tummino LLP

(57) ABSTRACT

A therapeutic agent delivery system includes a therapeutic agent delivery platform and a therapeutic guest agent. The therapeutic agent delivery platform is capable of being implanted in a tissue being treated. The platform includes a substrate and at least one host molecule coupled to the substrate. The therapeutic guest agent is capable of reversibly coupling with the host molecule when administered to the tissue being treated. The reversible coupling is defined by the binding affinity between the host molecule and the therapeutic guest agent. The therapeutic guest agent is delivered at a rate determined by the affinity release rate between the host molecule and the therapeutic guest agent. The degradation rate of the therapeutic guest agent may be slower than the affinity release rate between the host molecule and the therapeutic guest agent.

18 Claims, 18 Drawing Sheets

(56) References Cited

OTHER PUBLICATIONS

Hoare et al. Hydrogels in drug delivery: Progress and challenges. Polymer. 2008; 49: 1993-2007.*

Salmaso et al. Cyclodextrin/PEG based hydrogels for multi-drug delivery. Int J Pharm. Dec. 10, 2007;345(1-2):42-50.*

Binello et al. Synthesis of Cyclodextrin-Based Polymers and Their Use as Debittering Agents. Journal of Applied Polymer Science, 2008; vol. 107: 2549-2557.*

Vyas et al. Cyclodextrin based novel drug delivery systems. J Incl Phenom Macrocycl Chem (2008) 62:23-42.*

Li et al. Injectable drug-delivery systems based on supramolecular hydrogels formed by poly(ethylene oxide)s and alpha-cyclodextrin. J Biomed Mater Res A. May 1, 2003;65(2):196-202.*

Xu et al. Cyclodextrin-containing hydrogels for contact lenses as a platform for drug incorporation and release. Acta Biomaterialia 6 (2010) 486-493).*

Sugiura et al. Immobilized P-Cyclodextrins. Preparation with Various Crosslinking Reagents and the Guest Binding Properties. Bull. Cht:m. Soc. Jpn., 62, 1643-1651 (1989).*

Mocanu et al. Journal of Bioactive and Compatible Polymers. 2001; 16: 315-342.*

International Search Report for PCT/US2010/037183 dated Aug. 11, 2010.

Bibby et al., Mechanisms by which cyclodextrins modify drug release from polymeric drug delivery systems, International Journal of Pharmaceutics 197: 1-11 (2000).

Cheng et al., Synthesis of linear, β-cyclodextrin-based polymers and their camptothecin conjugates, Bioconjugate Chem. 14:1007-1017 (2003).

Van De Manakker et al., Cyclodextrin-based polymeric materials: synthesis, properties, and pharmaceutical/biomedical applications, Biomacromolecules 10(12): 3157-3175.

Fenyvesi , Cyclodextrin Polymers in the Pharmaceuticals Industry, Journal of Inclusion Phenomena, 6: 537-545 (1988).

Fenyvesi et al., Controlled Release of Drugs from CD Polymers Substituted with Ionic Groups, Journal of Inclusion Phenomena and Molecular Recognition in Chemistry, 25: 185-189 (1996).

Jenkins et al., Glossary of Basic Terms in Polymer Science, Pure & Appl. Chem, 86(12): 2287-2311 (1996).

Pun et al., Cyclodextrin-Modified Polyethylenimine Polymers for Gene Delivery, Bioconjugate Chem., 381-840 (2004).

Suh et al., A Novel Host Containing Both Binding Site and Nucleophile Prepared by Attachment of β-Cyclodextrin to Poly(ethylenimine), J. Am. Chem. Soc, 114: 7916-7917 (1992).

Szeman et al., Complexation of Several Drugs with Water-Soluble Cyclodextrin Polymer, Chem. Pharm. Bull., 35(1): 282-288 (1987).

Gref, R. et al., New self-assembled nanogels based on host-guest interactions: Characterization and drug loading, Journal of Controlled Release, 111: 316-324 (2006).

Thatiparti, T.R. and Von Recum, H.A., Cyclodextrin Complexation for Affinity-Based Antibiotic Delivery, Macromolecular Bioscience, 10: 82-90 (2010).

Allard, E. et al., Convection-enhanced delivery of nanocarriers for the treatment of brain tumors, Biomaterials, 30(12):2302-2318 (2009).

Gil-Alegre, M. et al., Three weeks release BCNU loaded hydrophilic-PLGA microspheres for interstitial chemotherapy: Development and activity against human glioblastoma cells, Journal of Microencapsulation, 25(8):561-568 (2008).

Hafeman, A. et al., Injectable Biodegradable Polyurethane Scaffolds with Release of Platelet-derived Growth Factor for Tissue Repair and Regeneration, Pharmaceutical Research, 25(10):1-28 (2008).

Harada, A. And Kamachi, M., Complex Formation between Poly-(ethylene glycol) and α-Cyclodextrin, Macromolecules, 23(10):2821-2823 (1990).

Husain, N. et al., Complexation of Doxorubicin with β- and γ-Cyclodextrins, Applied Spectroscopy, 46(4):652-658 (1992).

Kim, G. et al., Resorbable polymer microchips releasing BCNU inhibit tumor growth in the rat 9L flank model, Journal of Control Release, 123(2):172-178 (2007).

Lesniak, M. et al., Local delivery of doxorubicin for the treatment of malignant brain tumors in rats, Anticancer Research, 25(6B):3825-3831 (2005).

Sipos, E. et al., Optimizing interstitial delivery of BCNU from controlled release polymers for the treatment of brain tumors, Cancer Chemotherapy and Pharmacology, 39(5):383-389 (1997).

Thatiparti, T. et al. Cyclodextrin-based device coatings for affinity-based release of antibiotics, Biomaterials, 31(8):2335-2347 (2010).

* cited by examiner

THERAPEUTIC AGENT DELIVERY SYSTEM AND METHOD

CROSS-REFERENCE TO RELATED APPLICATION

This application claims benefit from U.S. Provisional Patent Application No. 61/183,698, entitled "Therapeutic Agent Delivery System and Method," filed on Jun. 3, 2009, which is hereby incorporated by reference in its entirety.

TECHNICAL FIELD

The present invention generally relates to a therapeutic system and a method for delivery, and more particularly to a therapeutic agent delivery system and related method for delivering a therapeutic agent to a desired location.

BACKGROUND OF THE INVENTION

In many drug delivery applications, including the delivery of therapeutic agents, proteins, and genes, it is desirable to provide both temporal and spatial control over drug delivery or durable presence of signaling molecules. A high level of spatio-temporal control is needed to maintain the concentration of the drug at the site of action at a therapeutic level while minimizing undesirable systemic side effects. In addition to providing both controlled and targeted drug delivery; for many applications there must also exist some mechanism for protecting the therapeutic agent from in vivo degradation and inactivation. Consequently, many drug delivery systems (DDSs) composed of drug encapsulated in degradable or non-degradable polymer matrices, and micro- or nanoparticles have been developed. Encapsulating the therapeutic agent in a polymer matrix not only protects the drug from degradation, but also allows for the delivery of a large drug payload, which can be released over an extended period of time.

Drug release from such systems is typically controlled by passive diffusion from the polymer matrix, or a combination of diffusion and matrix degradation. While based on passive mechanisms for providing control over drug delivery, these systems do afford a certain degree of tunability. By altering parameters such as the polymer composition or the crosslink density the degradation rate of the matrix can be controlled. The use of DDSs with multiple layers has also been examined as a means of providing finer control over drug release. Systems that offer an even greater degree of tunability by utilizing more active mechanisms for controlling drug delivery have also been developed. These systems often use external stimuli, such as pH, ionic strength, and/or temperature to further control drug release. However, all of these systems share a number of limitations, stemming from the lack of a selective interaction between the drug and the DDS, that greatly restrict their broad efficacy across a number of different applications.

Without the ability to form selective interactions between the drug and DDS, the ability to tune the system becomes a function of the properties of the polymer matrix (e.g., pore size, degradation rate, sensitivity to changes in pH, ionic strength, or temperature, etc.), which often necessitates the development of multiple designs to meet different applications. This limitation is both inefficient and time consuming, and demonstrates the need for the development of a general platform that can be tuned to different applications independently of its properties. Furthermore, while many of the systems previously described can be used to provide control over the release of a single agent, they are limited in their ability to selectively control the release of multiple agents. The ability to selectively control the release, and thus expression, of multiple agents is especially important in tissue engineering applications that intend to recapitulate the natural tissue regeneration process. In such applications, the DDS must be able to express different bioactive agents at different time points. Thus, the DDS must contain some mechanism for providing selective control over the release of multiple agents. Finally, for the majority of implantable DDSs the drug reservoir is limited. While this may be acceptable, or even desirable for some applications, it is a major drawback for the treatment of chronic conditions (e.g. insulin delivery in diabetes). For such applications, a reloadable drug reservoir is needed. This presents a complicated design criterion as the DDS must be able to selectively interact with and bind the desired drug molecule(s) from the surrounding environment.

SUMMARY OF THE INVENTION

The present invention relates to a therapeutic agent delivery system that includes a therapeutic agent delivery platform and a therapeutic guest agent. The therapeutic agent delivery platform is capable of being implanted in a tissue being treated. The platform includes a substrate and at least one host molecule coupled to the substrate. The therapeutic guest agent is capable of reversibly coupling with the host molecule when administered to the tissue being treated. The reversible coupling is defined by the binding affinity between the host molecule and the therapeutic guest agent. Depending on the nature of this reversible coupling, two scenarios can be realized. If the degradation rate of the therapeutic guest agent is slower than the affinity release rate between the host molecule and the therapeutic guest agent, then once the agent is released from the coupling, it will be available for therapeutic delivery elsewhere in the body (e.g. antibiotics, chemotherapy, etc.). If the degradation of the agent is faster than the release rate, then the reversible coupling can be used for the durable presence of a signaling molecule on a material or device (e.g. heparin, RGD, etc.). The therapeutic agent delivery platform is a capable of being reloaded with additional therapeutic agent after release of the therapeutic agent to the tissue being treated.

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION

Figure 1:
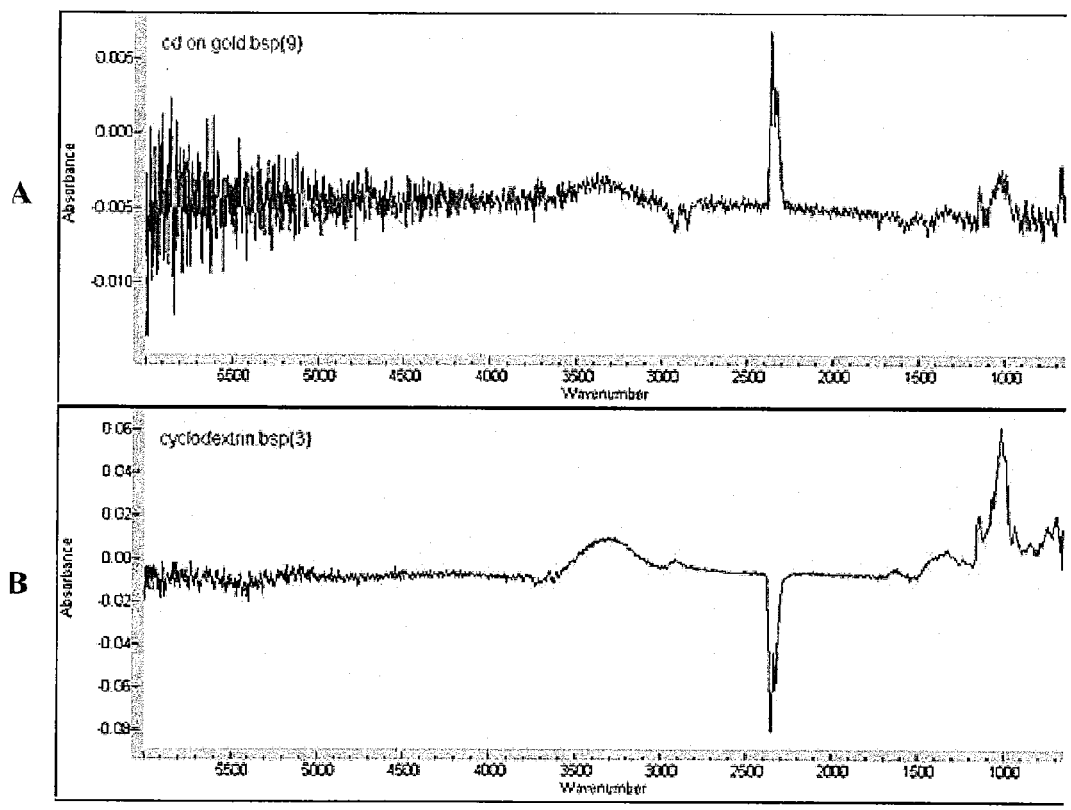
FIGS. 1A-B are ATR-FTIR spectra of cyclodextrin (CD) deposited on a gold substrate. CD-SH was dissolved in ethanol at a 1 mM concentration. Then either 100 µl was dried on the surface (FIG. 1A) or briefly dropped onto the surface, then removed and extensively washed to remove any unbound molecules (FIG. 1B). The presence of characteristic CD absorbance profiles (peaks at 3300, 1300 and 1100) in the washed sample demonstrates binding of the —SH group to the gold surface.

The present invention generally relates to a therapeutic system, and more particularly to a therapeutic agent delivery system. The therapeutic system of the present invention includes a therapeutic guest agent and a therapeutic guest agent delivery platform. The therapeutic guest agent can selectively and reversibly interact with the therapeutic guest agent delivery platform to provide finer control over therapeutic agent loading and release profiles.

In particular, the therapeutic guest agent may selectively and reversibly interact with the host molecule in the therapeutic guest agent delivery platform. The ability to form selective and reversible interactions between the therapeutic guest agent and the therapeutic guest agent delivery platform affords a number of advantages over systems that employ nonselective methods for controlling drug loading and release. By altering the type of interaction, the number of interactions, as well as the concentration and geometries of the therapeutic guest agent and the therapeutic guest agent delivery platform, in particular the host molecule, it is possible to achieve a variety of loading and release kinetics, ranging from low affinity, reversible interactions to interactions, with such high affinity that they are essentially irreversible within the lifetime of the patient or device, resulting in the durable presence of that molecule on that material. Individual interactions can also be multiplexed on a given molecule resulting in a change from low affinity to high affinity.

Additionally, the use of selective interactions between the therapeutic guest agent and the therapeutic guest agent delivery platform, in particular the host molecule, presents a facile means for providing targeted drug delivery. The loading and release kinetics of the therapeutic guest agent with the therapeutic guest agent delivery platform allows the therapeutic guest agent delivery platform to be selectively refilled or reloaded with additional therapeutic guest agents after the therapeutic guest agent has been delivered to the desired area.

A therapeutic agent delivery platform may comprise a substrate and a host molecule. The platform may be capable of, but is not limited to, being implanted in a tissue of a subject. As described in more detail below, a therapeutic guest agent, such as a polypeptide, a polynucleotide, a small molecule, an antibiotic, a steroid or an imaging agent, can include a portion capable of reversibly complexing with a host molecule attached to the substrate. Unlike other therapeutic agent delivery systems which rely solely on diffusion for therapeutic agent delivery, the reversible complexing of the host molecule and the therapeutic guest agent of the present invention is governed by molecular affinity interactions so that the degradation rate of the therapeutic guest agent may be slower than the affinity release rate of the therapeutic guest agent from the host molecule.

The therapeutic agent delivery platform may include a substrate and at least one host molecule coupled to the substrate. In one embodiment, the substrate may comprise, but is not limited to, a plurality of particles. The particles may be sized so that the particles remain substantially implanted in a desired area such as, but not limited to, tissue and do not migrate as a result of fluid flow such as, but not limited to, blood through the desired area. For example, the particles may be dimensioned so that the particles remain substantially implanted in the tissue and do not migrate to a tissue or tissues not being treated. Depending upon the particular type and location of the tissue, the particles can be dimensioned to have nanoscale (i.e., nanoparticles) or microscale (i.e., microparticles) sizes.

Where the particles comprise microparticles, for example, the microparticles can have a diameter less than about 1 mm, and typically between about 1 and 200 microns. Alternatively, where the particles comprise nanoparticles, the nanoparticles can have a diameter ranging from about less than 1 nanometer to about 1 micron. Both microparticles and nanoparticles may have, but are not limited to, an approximately spherical geometry and can be of fairly uniform size. It will be appreciated that the particles may also be larger or smaller than nanoscale or microscale sizes depending upon the particular application of the present invention.

In another embodiment the therapeutic delivery platform may be comprised of a host molecule, a substrate, or a combination thereof. The host molecule can include any molecule capable of reversibly complexing with the therapeutic guest agent such as, but not limited to, cyclic oligosaccharides. In one example of the present invention, the host molecule can comprise a CD molecule, such as an α-cyclodextrin molecule, a β-cyclodextrin molecule, a γ-cyclodextrin molecule, or a derivative thereof. As used herein, the terms "cyclodextrin" or "CD" can refer to cyclic carbohydrate molecules having six, seven, or eight glucose monomers arranged in a donut shaped ring and which are denoted α-, β-, or γ-cyclodextrin, respectively. The terms can also refer to both unmodified and modified CD monomers and polymers (i.e., CD derivatives). CD is a ring of 6-8 glucose molecules whose bonds align to form a ring-like structure having a hydrophobic pocket and a highly hydrophilic exterior. Hydrophobic small molecules can fit into the pocket of CD molecules and enter solution at a much higher concentration. Due to the reversible nature of this hydrophobic interaction, the small molecules can remain unmodified (i.e., not degraded) and can be released from the hydrophobic pocket based on molecular affinities and/or association/dissociation kinetics to exert their therapeutic effect(s).

In another embodiment the host molecule may be chemically modified CD's such as, but not limited to, hydroxypropyl-CD. The chemically modified CD may be selected due to its affinity to certain therapeutic agents.

It will be appreciated that the host molecule can include a variety of other molecules including antibodies, antibody fragments, antigens, heparin, polynucleotides, receptor proteins, avidin, streptavidin, and magnetic particles. Host molecules comprising antibodies can include whole antibodies e.g., of any isotype (IgG, IgA, IgM, IgE, etc.) and fragments thereof which are specifically reactive with a target agent. Antibodies can be fragmented using conventional techniques, and the fragments screened for utility and/or interaction with a specific epitope of interest. Thus, antibodies can include segments of proteolytically-cleaved or recombinantly-prepared portions of an antibody molecule that are capable of selectively reacting with a certain target agent. Non-limiting examples of such proteolytic and/or recombinant fragments include Fab, F(ab')2, Fab', Fv, and single chain antibodies (scFv) containing a V[L] and/or V[H] domain joined by a peptide linker. The scFv's may be covalently or non-covalently linked to form antibodies having two or more binding sites. Antibodies can also include polyclonal, monoclonal, or other purified preparations of antibodies, recombinant antibodies, monovalent antibodies, and multivalent antibodies. Antibodies may be humanized, and may further include engineered complexes that comprise antibody-derived binding sites, such as diabodies and triabodies.

Host molecules comprising polynucleotides can include oligonucleotides, nucleotides, or a fragment thereof, DNA or RNA (e.g., mRNA, rRNA, tRNA) of genomic or synthetic origin and which may be single- or double-stranded and may represent a sense or antisense strand, peptide nucleic acids, or any DNA-like or RNA-like material of natural or synthetic origin including, e.g., iRNA and ribonucleoproteins (e.g., iRNPs).

Host molecules comprising receptors can include any protein or polypeptide having a molecular structure which is generally characterized by the selective binding of a specific substance (e.g., a ligand, receptor, or other binding domain). Exemplary receptors can include, for example, cell-surface receptors for peptide hormones, neurotransmitters, antigens, complement fragments, immunoglobulins, and cytoplasmic receptors for steroid hormones.

Host molecules can also include avidin, streptavidin, or their derivatives. Avidin (a glycoprotein from chicken egg white) and streptavidin (from *Streptomyces avidinii*) are two related proteins that bind biotin with similar dissociation constants of about $10^{-15}$ M. Avidin occurs naturally in a tetrameric form with four identical subunits, each having about 128 amino acid residues, six mannose residues, and three glucosamine residues, for a combined molecular weight of approximately 68,000. In addition to the ability of avidin and streptavidin to bind biotin, many of their physical properties are quite similar. For example, both are constructed of four non-covalently attached identical subunits, each of which bears a single biotin-binding site. The subunit $M_r$ values are very similar. Moreover, several short stretches in the sequences of the two proteins are preserved, particularly two Trp-Lys stretches that occur at approximately similar positions.

Avidin, streptavidin, and their derivatives, as well as methods for obtaining such molecules, are within the purview of those skilled in the art. For example, modified avidins have been prepared, such as N-acyl avidins, e.g., N-formyl, N-acetyl and N-succinyl avidins. These derivatives of avidin reduce the charge of the protein, but they may all be prepared via covalent attachment to the available lysines of avidin. An alternative to lysine modification is the modification of arginines on avidin. In this case, the lysines are still available for subsequent interaction. Two different derivatives of avidin which are modified in this manner are commercially available. One, EXTRAVIDIN, can be obtained in various functionally derivatized or conjugated forms from Sigma Chemical Company (St. Louis, Mo.). A second, NEUTRALITE AVIDIN (a product of Belovo Chemicals, Bastogne, Belgium), is a deglycosylated form of avidin obtained enzymatically, which exhibits a neutral pH and bears free lysine groups for further derivatization. Other avidin derivatives include those disclosed in U.S. Pat. Nos. 6,638,508 and 6,632,929, the entire disclosures of each of which are incorporated by reference herein.

Host molecules can additionally or alternatively include magnetic particles or beads. Magnetic particles or beads can comprise particulate material having a magnetically responsive component. Examples of magnetically responsive materials can include ferromagnetic, paramagnetic, and superparamagnetic materials. Magnetic particles or beads are known in the art and can include, for example, those described in U.S. Patent Pub. Nos. 2007/0225488 A1, 2005/0272049 A1, 2004/0132044 A1, and U.S. Pat. No. 7,078,224.

When selecting a host molecule the mechanical properties of the chosen host molecule may be modified to achieve a desired mechanical property for an affinity based delivery system. Modifying the mechanical properties of a host molecule may modify the release rate of the therapeutic guest agent to the desired level. Examples of methods to modify the host molecule mechanical properties include, but are not limited to, chemical grafting of the host molecule, attaching the host molecule to the backbone of a polymer, and creating a host molecule polymer by crosslinking the host molecule or short chains thereof. Examples of mechanical properties that may be modified include, but are not limited to, stiffness, strength, ductility, brittleness, malleability, plasticity, elasticity, toughness, hardness, and combinations of two or more thereof.

In one embodiment a host molecule, such as CD, may be chemically grafted onto a substrate. This substrate may include, but is not limited to, gold, glass, iron-based metals, titanium, polymers, polyester, and combinations of two or more thereof. The mechanical properties of the host molecule become similar to that of the chosen substrate. In addition, the mechanical properties may also have a limited capacity to change.

In another embodiment a host molecule, such as CD, is attached to the backbone of another polymer. This polymer may include, but is not limited to, polyvinyl alcohol, poly(acrylic acid), or a combination of two or more thereof. The mechanical properties of the host molecule become similar to that of the chosen polymer. In addition, the mechanical properties may also have a limited capacity to change.

In another embodiment CD polymers are created by crosslinking CD or short chains thereof. In one specific embodiment, the selected CD may be, but is not limited to, β-cyclodextrin and it may be crosslinked at room temperature in which the method of crosslinking has aspects of physical crosslinking and chemical crosslinking. Adjusting the nature of the above method may create materials of different levels of stiffness to provide the desired stiffness. This method is capable of forming polymers with a range of mechanical properties. To achieve desired results it is possible to change either the chemical nature of the crosslinker, the chemistry of the crosslinker, changing the crosslinker length, or a combination of two or more thereof. Examples of possible chemical natures of a crosslinker include, but are not limited to, a mono-functional crosslinker, a di-functional crosslinker, a trifunctional crosslinker, or a combination of two or more thereof. Examples of possible crosslinker chemistry include, but are not limited to, isocyanate chemistry, carbodiimide chemistry, succinimide chemistry, maleimide chemistry, and any other crosslinker chemistry known in the art. Examples of methods to obtain a desired crosslinker length include, but are not limited to, using short and long chains of PEGs as bifunctional crosslinkers. The length of the PEG molecule affects the mechanical properties, such as stiffness, of the host molecule.

The substrate to which the host molecule is coupled may comprise a polymer. In one embodiment, the polymer may be positively-charged and/or biocompatible. In one embodiment, the polymer may be formed from any one or combination of known polymerizable monomers. Biocompatible polymers may include any polymer moiety that is substantially non-toxic and does not tend to produce substantial immune responses, clotting, or other undesirable effects. Examples of suitable biocompatible polymers may include, but are not limited to, polyalkylene oxides, polymethacrylates, polyurethanes, cellulosics, polyhydroxyalkyl acrylates, polyesters, and the like, and combinations of two or more thereof. Other examples of biocompatible polymers may include, but are not limited to, polymers comprised of at least one polyethylene monomer, such as polyethylene glycol (PEG) or polyethylene oxide, polymers comprised of polyamine monomers, such as polyethyleneimine (PEI), and poly(L-lactide) (PLLA), poly-p-dioxanone (PDO), polycaprolactone (PCL), polyvinyl alcohol (PVA), poly(lactide-co-glycolide) (PLG), and the like, and combinations of two or more thereof.

The substrate may also comprise at least one of, but is not limited to, antibodies, antibody fragments, antigens, heparin, integrins, polynucleotides, receptor proteins, avidin, streptavidin, magnetic particles, and the like.

Host molecules may be coupled directly with the polymer via any one or combination of known molecular interactions, including electrostatic interactions, metal coordination, covalent bonding, non-covalent interactions, hydrophobic interactions, hydrogen bonding, ionic forces, van der Waals forces and combinations of two or more thereof. It will be appreciated that the polymer, the host molecule, or both, can be chemically modified to modulate the molecular interaction(s) between the polymer surface and the host molecule. By adding a known functional group to the surface of the polymer that binds a particular host molecule, for example, the molecular interaction(s) between host molecules and the surface of the polymer can be increased.

In one example of the present invention, a CD molecule may be coupled directly with the polymer via electrostatic interactions between the negatively-charged hydroxyl groups of the CD molecule and the positively-charged polymer. The CD molecule can also be chemically modified to facilitate coupling of the CD molecule with the polymer by replacing, for example, a hydroxyl group of the CD molecule with a thiol group. Additionally or alternatively, a bifunctional cross-linker, such as PMPI can be used to facilitate coupling of the CD molecule and the polymer. Other methods of chemically coupling a host molecule to a surface can include CD-thiols attaching to gold, CD-silanes attaching to glass and/or ceramics, CD-phosphates attaching to titanium, and CD-catechols or other diols attaching to iron-containing compounds (e.g., steel).

In one embodiment, the therapeutic guest agent may include a portion for coupling to a portion of the host molecule. The portion of the therapeutic guest agent and/or the portion of the host molecule may include, but is not limited to, a portion of a molecule, a hydrophobic linker coupled to the therapeutic guest agent, or a combination thereof. In one embodiment, the therapeutic guest can include a hydrophobic portion for coupling to a CD molecule.

A therapeutic guest agent may be any agent that is desired to be provided to a specific area, as released by the host molecule. Such therapeutic guest agents may include, but are not limited to, polypeptides (e.g., growth factors, antibodies, etc.), polynucleotides, small molecules, and imaging agents, and combinations of two or more thereof. The therapeutic agent delivery system may also include more than one therapeutic guest agent that are the same as or different from the other therapeutic guest agents. The therapeutic guest agent may also comprise any one or combination of two or more of the following:

Alkaloids including, but not limited to, docetaxel, etoposide, irinotecan, paclitaxel (TAXOL), teniposide, topotecan, vinblastine, vincristine, and vindesine;

Alkylating agents including, but not limited to, busulfan, improsulfan, piposulfan, benzodepa, carboquone, meturedepa, uredepa, altretamine, triethylenemelamine, triethylenephosphoramide, triethylenethiophosphoramide, chlorambucil, chloranaphazine, cyclophosphamide, estramustine, ifosfamide, mechlorethamine, mechlorethamine oxide HCl, melphalan novemebichin, perfosfamide phenesterine, prednimustine, trofosfamide, uracil mustard, carmustine, chlorozotocin, fotemustine, lomustine, nimustine, semustine ranimustine, dacarbazine, mannomustine, mitobronitol, mitolactol, pipobroman, and temozolomide;

Antibiotics and analogs thereof including, but not limited to, aclacinomycins, actinomycins, anthramycin, azaserine, bleomycins, cactinomycin, carubicin, carzinophilin, cromomycins, dactinomycins, daunorubicin, 6-diazo-5-oxo-1-norleucine, doxorubicin, epirubicin, idarubicin, menogaril, mitomycins, mycophenolic acid, nogalamycine, olivomycins, peplomycin, pirarubicin, plicamycin, porfiromycin, puromycine, streptonigrin, streptozocin, tubercidin, zinostatin, and zorubicin;

Antimetabolites including, but not limited to, denopterin, edatrexate, mercaptopurine (6-MP), methotrexate, piritrexim, pteropterin, pentostatin (2'-DCF), tomudex, trimetrexate, cladribine, fludarabine, thiamiprine, ancitabine, azacitidine, 6-azauridine, carmofur, cytarabine, doxifluridine, emitefur, floxuridine, fluorouracil, gemcitabine, tegafur, hydroxyurea and urethan;

Platinum complexes including, but not limited to, caroplatin, cisplatin, miboplatin, and oxaliplatin;

Pyrimidine and purine antagonists including, but not limited to, fluorouracil (5-FU), fluorodeoxyuridine (5-FUDR), azacytidine (5-AZC), 6-thioguanine (6-TG), chlorodeoxyadenosine (2-CDA); and Other agents including, but not limited to, aceglatone, amsacrine, bisantrene, defosfamide, demecolcine, diaziquone, eflornithine, elliptinium acetate, etoglucid, etoposide, fenretinide, gallium nitrate, hydroxyurea, lonidamine, miltefosine, mitoguazone, mitoxantrone, mopidamol, nitracrine, pentostatin, phenamet, podophillinic acid 2-ethyl-hydrazide, procarbazine, razoxane, sobuzoxane, spirogermanium, teniposide tenuazonic acid, triaziquone, and 2,2',2"-trichlorotriethylamine.

In another embodiment, the therapeutic guest agent may comprise DNA or RNA, or a therapeutic molecule using DNA or RNA as a coupling agent. In one embodiment, when the therapeutic guest agent comprises RNA the RNA polynucleotide can include a siRNA, a microRNA, a sense RNA, an anti-sense RNA, a ribozyme, or a combination of two or more thereof. In another embodiment, when the therapeutic guest agent comprises a DNA plasmid the plasmid may include a therapeutic polynucleotide encoding a therapeutic polypeptide. It will be appreciated that the therapeutic polynucleotide can include any desired gene or gene fragment capable of promoting or causing a desirable cellular effect. In one embodiment, the desirable effect may be tumor suppression but the desirable effect may be any desirable effect known in the art. In one embodiment, when the desirable effect is tumor suppression, the therapeutic agent may be a therapeutic polynucleotide that may include a tumor suppressor gene, a chemokine gene, a cytokine gene, an antigenic gene, a cytotoxic gene, a cytostatic gene, an apoptotic gene (i.e., a pro-apoptotic gene), an anti-angiogenic gene, or a combination of two or more thereof.

In another embodiment, the therapeutic guest agent may comprise any bioactive agent capable of arresting cancer or tumor cell growth, inducing apoptosis of a cancer or tumor cell, and/or labeling a cell (cancerous or non-cancerous) in which the bioactive agent is present or otherwise associated with, inducing an immune response in a subject, arresting or preventing microbial growth and/or proliferation, and increasing or decreasing transcription or translation in a cell.

In another embodiment the therapeutic guest agent may also include an imaging agent. Generally, an imaging agent may include any compound used to detect, image and/or monitor the presence and/or progression of a condition(s), pathological disorder(s) and/or disease(s). Imaging agents may be used for any use known in the art such as, but not limited to, studying a wide range of physiologic processes, disease diagnosis, disease prognosis, diagnostic procedures, and the broader study of biological systems.

The substrate of the therapeutic agent delivery system may be selectively varied or modified to control the temporal and spatial delivery aspects of the therapeutic guest agent. The distribution (e.g., the number) of host molecules coupled with the substrate can be increased or decreased depending upon the desired spatial and temporal release profile for a given therapeutic guest agent (or agents). For example, a greater number of host molecules can be coupled with the surface of the substrate to promote a higher concentration, and thus spatial distribution, of therapeutic guest agents.

In one embodiment, the affinity interaction between the therapeutic agent and the host molecule may depend on the type of host molecule selected and the size of the hydrophobic molecules present in the therapeutic guest agent. In addition, the affinity interaction may differ because of the differing pocket sizes in the host molecule. The differing pocket sizes enable the host molecule to accommodate various sizes of therapeutic guest agent molecules with varying release rates. The release rate of the therapeutic guest agent may depend on the affinity interaction between the therapeutic guest agent and the host molecule. In one specific embodiment the therapeutic guest agent release rate may depend on how the therapeutic guest agent fits in the pocket.

In one embodiment, α-cyclodextrin, which has the smallest cavity size of the group containing a α-cyclodextrin molecule, β-cyclodextrin molecule, and γ-cyclodextrin molecule, may accommodate smaller portions of hydrophobic groups present in a therapeutic guest agent or a hydrophobic unit having a similar size as that of the cavity size of the α-cyclodextrin. While γ-cyclodextrin has the largest cavity size that can accommodate larger hydrophobic groups if present in the therapeutic guest agent. β-cyclodextrin cavity size falls in between α-cyclodextrin and γ-cyclodextrin and accommodates accordingly.

In another embodiment, the therapeutic guest agent delivery platform may be selected due to the stiffness of the therapeutic delivery platform. In one embodiment, therapeutic guest agent delivery platforms with low stiffness may include, but are not limited to gels such as hydrogels. Stiffness in a therapeutic delivery platform may be changed by a variety of ways. Examples of ways to modify stiffness in a therapeutic delivery platform include, but is not limited to, the time of crosslinking, type of crosslinker, size of crosslinker, concentration of crosslinker, chemical conjugation, and the number/type of physical interaction such as, but not limited to, clay or ionic charge interactions.

In one example, the stiffness of the room temperature crosslinked gels is proportional to the time of crosslinking. The longer the time of crosslinking, the greater the stiffness of the gel. In another example, gel stiffness may also be dependent on the type of crosslinker. A branched crosslinker gives gels that have less stiffness while linear hydrophobic crosslinkers give gels with more stiffness. In one embodiment, in linear hydrophobic crosslinkers, hydrophobic interactions within the crosslinker as well as with CD molecules may lead to increased stiffness of the gels. In one embodiment, the above crosslinking may be possible in gels crosslinked at room temperature and is the result of allowing enough time for conformational change to occur, the formation of hydrogen bonds, and hydrophobic interactions. The above combinations may have a dramatic effect on stiffness and therefore modulate CD measured stiffness from kPa to MPa.

In one embodiment, for orthopedic applications, the desired stiffness falls in the range of kPa to MPa.

In one embodiment, when the therapeutic guest agent is a hydrophobic drug the affinity-based release may depend on either one of or both the structure of the therapeutic agent and the stiffness of the therapeutic delivery platform. In one example, if the therapeutic guest agent is a drug that fits exactly within a host molecule pocket, such as CD, and is coupled with a stiffness that is high enough, it may be very difficult for the drug to escape from the therapeutic delivery platform as the interaction between the drug and host molecule is intensified.

Other ways to alter the chemical nature of the pocket include, but are not limited to, using other kinds of molecular affinity interactions such as protein-protein interactions such as receptor-ligand interactions and antibody-antigen interactions, using oligonucleotide interactions of complimentary strands, using heparin-growth factor interactions, using avidin-biotin interactions, and other similar interactions known in the art.

To further modulate delivery and release of therapeutic guest agents to and from host molecules, therapeutic guest agents can be chemically modified with a tuning molecule. By altering the type of monovalent interaction, the number of interactions, as well as the concentration and geometry of both the host and therapeutic guest molecules, it is possible to modulate or fine-tune the binding strength, and thus the kinetics, of the host molecule-therapeutic guest agent interaction so that the complete range from highly-reversible monovalent interactions to highly-stable (and even irreversible) polyvalent interactions can be achieved. For example, by tethering multiple monovalent therapeutic guest agents together using a tuning molecule to form a multivalent therapeutic guest agent, it is possible to increase the overall binding affinity (i.e., the avidity) between a host molecule and a therapeutic guest agent.

The release rate may be altered by changing the chemical nature of the therapeutic agent or by inserting an inert molecule that fits within the host molecule but can be conjugated to the therapeutic guest agent. This allows any therapeutic guest agent to be used with an affinity-based system, even if that therapeutic guest agent has no affinities itself. In one embodiment, multiple inert molecules may be connected to a therapeutic guest agent to change the release rate to the desired result.

The release rate of the therapeutic guest agent is minimally affected by the thinness of the therapeutic delivery platform.

Therapeutic guest agents may contain multiple affinity domains. Therapeutic agents may be modified so the therapeutic guest agent has a higher binding constant compared to its pure form. In one example, rifampin, a specific antibiotic, may be modified that results in a drug version that has a higher binding constant compared to the pure antibiotic.

More than one therapeutic delivery platform may be used at a time. In one embodiment, at least two separate host molecules may be tuned to have at least two different therapeutic guest agents release at desired rates from a device. Such as, but not limited to, a small therapeutic guest agent being released from a small pocket from a host molecule and a larger therapeutic guest agent being released from a larger pocket from a second host molecule. In one example, this may be used for the synergistic release of at least two antibiotics, but may also be used for two anticancer drugs, or two of any other therapeutic guest agent listed.

The tuning molecule may include a hydrophobic molecule, such as adamantane (or a portion thereof) that is capable of coupling with a hydrophobic portion of a host molecule (e.g., the hydrophobic pocket of a CD molecule). Adamantane consists of four cyclohexanes fused to each other in chair conformations. Because adamantane is generally hydrophobic, an adamantane molecule (or a portion thereof) can be readily coupled with both the hydrophobic pocket of a CD molecule and a therapeutic guest agent. A hydrophobic tuning molecule, such as adamantane can facilitate coupling of less hydrophobic and/or hydrophilic therapeutic guest agents with host molecules that may not readily couple with a hydrophobic portion of a host molecule. In one example, as the number of adamantane molecules increase per therapeutic guest agent molecule, less therapeutic guest agent is released. The tuning molecule may consist of adamantane or more suitable hydrophobic units that have a higher binding constant with the selected host molecule to improve the sustained release properties of the therapeutic guest agents.

In one embodiment, enough tuning molecule may be added to the host molecule to make the affinity between the host molecule and the therapeutic guest agent so high that the therapeutic guest agent essentially never releases before the therapeutic guest agent degrades. In one example, in an experimental drug using CD as the host molecule and adamantane as the tuning molecule, the above result was reached with about 6 adamantane groups per drug molecule. This high affinity situation may be used in examples such as, but not limited to, self-assembling bioactive agents on the surface of an implant, refilling, renewing, and reloading similar to the drug delivery version.

It will be appreciated that the tuning molecule can comprise other molecules capable of facilitating coupling between the therapeutic guest agents and the host molecules. For example, stimuli response polymers, such as NIPAAm can be coupled with the therapeutic guest agents to permit selective release of the therapeutic guest agents from the host molecules. NIPAAm molecules contain a hydrophilic group (i.e., an amido-group) and a hydrophobic group (i.e., an isopropyl-group). NIPAAm molecules can change their overall hydrophobicity or hydrophilicity in response to a change in temperatures above or below a critical temperature of about 32° C. For example, a temperature of about 37° C. can yield generally hydrophobic NIPAAm molecules, while a temperature of about 25° C. can yield generally hydrophilic NIPAAm molecules. By selectively adjusting the temperature, the hydrophobicity or hydrophilicity of NIPAAm molecules coupled with therapeutic guest agents can be manipulated so that the NIPAAm molecules are coupled with host molecules at body temperature (i.e., 37° C.) and can then be released from the host molecules at a temperature of about 25° C.

Besides providing a means for coupling therapeutic guest agents with host molecules, the tuning molecule can also be used to establish a gradient release profile for the therapeutic guest agents. For example, a therapeutic guest agent can be coupled to a plurality of tuning molecules so that the tuning molecules couple with a respective plurality of host molecules. With this arrangement, release of the tuning molecules from the host molecules permits only the release of the therapeutic guest agent and thus a slower release profile (as compared to a single therapeutic guest agent/tuning molecule complex) can be established.

Release of the therapeutic guest agents from host molecules can also be selectively controlled by flooding implanted substrates of the therapeutic agent delivery platform with tuning molecules. Where therapeutic guest agents are coupled with hydrophobic tuning molecules, for example, a plurality (i.e., excess) of non-coupled hydrophobic tuning molecules can be contacted with the implanted particles. Contacting the implanted particles with an excess of hydrophobic tuning molecules can dislodge or separate the therapeutic guest agents from the host molecules and cause the release of the therapeutic guest agents.

Additionally, release of the therapeutic guest agents from host molecules can be selectively controlled by flooding implanted particles with additional and/or different therapeutic guest molecules having greater hydrophobicitites. For example, implanted substrates can be flooded with therapeutic guest agents that are more hydrophobic than the therapeutic guest agents already coupled with host molecules. Consequently, the therapeutic guest molecules having a greater hydrophobicity can displace the less hydrophobic therapeutic guest molecules from the host molecules.

Advantageously, once the therapeutic agent has been released to the tissue being treated, the therapeutic agent delivery platform can be reloaded or refilled with additional therapeutic agents for subsequent or continuing treatment of the tissue. The therapeutic agent delivery platform can be refilled by contacting the therapeutic agent delivery platform with an additional concentration of therapeutic agents. Delivery of the therapeutic agent to the therapeutic agent delivery platform can be performed, for example, by direct injection of the therapeutic agent at the tissue site the substrate is implanted or by systemic administration of therapeutic agent to the subject. The binding affinity of the therapeutic agent to the host molecules can be such that the therapeutic agent localizes to the therapeutic agent delivery platform after systematic administration to the subject remains localized at the tissue being treated.

In an example of the present invention, a host molecule comprising CD can be made suitable for coupling to at least one surface of a polymer by first converting one of the hydroxyl groups of the CD molecule into a thiol group. This can be done by mixing about 0.300 g of 6-Tosyl-β-CD and about 0.300 g of thiourea (at about 1:16.5 molar ratio) in a 50 ml round bottom flask. Next, about 15 ml of about 80% methanol can be added to the flask. The mixture can then be heated under reflux for about 2 days at about 100° C. The mixture can be evaporated in a vacuum, whereafter about 4.5 ml of 100% methanol can be added and refluxed for about 1 hour. The solid can be filtered and dissolved in about 10.35 ml of about 10% NaOH at about 50° C. for about 5 hours. The pH of solution can be adjusted to about 2 using about 10% HCl. Next, about 0.750 ml of Trichloroethylene can be added and stirred overnight. The resulting precipitate can then be filtered and washed with water. The precipitate can be evaporated in a vacuum, followed by repeated recrystallization from water.

After converting one of the hydroxyl groups of the CD molecule to a thiol group, the thiol-modified CD molecule can optionally include a bifunctional cross-linker, such as PMPI. This can be done by dissolving about 0.750 g of EVOH in about 14 ml of DMSO. Next, about 50 mg (0.23 mmol) of PMPI can be dissolved in about 1 ml of DMSO. This solution of PMPI in DMSO can then be added to the polymer melt. The solution can react for about 3 hours at about room temperature under constant stirring.

About 12.5 mg (0.024 mmol) of the thiol-modified CD molecule can then be dissolved in about 1.25 ml of about 0.1 M NaOH (in DMSO) and incubated at about room temperature for approximately 15 minutes. About 17.5 µl of about 6 M HCl can then be added in order to neutralize the solution. The solution can be buffered with about 0.25 ml of about 0.5 M sodium phosphate. The pH of the solution can then be adjusted to approximately 7 using about 6 M HCl.

About 10 ml of the EVOH-PMPI solution in DMSO can then be removed and placed in a glass vial. The activated, thiol-modified CD molecule can then be added to the remaining 5 ml of EVOH-PMPI solution in DMSO. The solution can react for about 8 hours at about room temperature and under constant stirring. The resulting pEVOH/thiol-modified CD molecule mixture can then be electrospun into nanofiber meshes as disclosed by Kenawy et al., "Electrospinning of poly(ethylene-co-vinyl alcohol) fibers" (2003); *Biomaterials* 24(6):907-913.

In another example of the present invention, a therapeutic agent delivery system can comprise a polymer coupled with a heparin or heparin sulfate host molecule and a therapeutic guest agent comprising a growth factor, such as IL-7. The heparin host molecules can be chemically attached to the polymer or entangled within the polymer so that the heparin molecules do not detach before the IL-7 molecules are released from the heparin molecules. Such a therapeutic agent delivery system may be useful in treating a variety of diseases or conditions. To treat HIV/AIDS, for example, the therapeutic agent delivery system can be administered to a subject who is either infected with or suspected of having HIV/AIDS. Once administered to the subject, the IL-7 molecules can be degraded at a rate that is slower than the affinity release rate of IL-7 from the heparin molecules. Degradation and release of IL-7 in this manner can augment T cell response and thereby help to prevent or suppress HIV infection/AIDS. IL-7 can be periodically re-administered to the subject to "re-fill" the heparin host molecules and thereby maintain a substantially uniform release rate of IL-7 into the subject.

In accordance with another aspect of the present invention, a method for delivering a therapeutic agent by placing a therapeutic agent delivery system at a desired location. The therapeutic agent delivery system can comprise a therapeutic agent delivery platform. Therapeutic agent delivery platform can have a substrate and at least one host molecule coupled to the substrate. The therapeutic agent delivery system can also comprise a therapeutic guest agent capable of reversibly complexing with the host molecule when administered to the tissue being treated. The therapeutic guest agent may have a degradation rate that is slower than the affinity release rate of the therapeutic guest agent from the host molecule.

In accordance with another aspect of the present invention, a method for treating a tissue of a subject may comprise administering a therapeutic agent delivery system to a tissue target site in the subject. The therapeutic agent delivery system can comprise a therapeutic agent delivery platform. Therapeutic agent delivery platform can have a substrate and at least one host molecule coupled to the substrate. The therapeutic agent delivery system can also comprise a therapeutic guest agent capable of reversibly complexing with the host molecule when administered to the tissue being treated. The therapeutic guest agent may have a degradation rate that is slower than the affinity release rate of the therapeutic guest agent from the host molecule.

The target tissue site can comprise any anatomical location of the subject. Examples of target tissue sites can include tissue, such as connective tissue, epithelium, muscle, and nervous tissues, as well as tumors, organs, lymph nodes, individual cells, arteries and veins. Target tissue sites can also comprise intravascular locations, such as an intra-arterial site, as well as intraluminal locations, such as a portion of the esophagus or bile duct. The implantable therapeutic agent delivery system can be implanted at the target tissue site using any known surgical, transvascular, percutaneous, and/or minimally invasive technique.

In one example, the substrate can include a plurality of particles that are formed by electrospinning. Methods for electrospinning monomers to form three-dimensional polymer-based materials are known in the art. Generally, electrospinning uses an electrical charge to form a mat of fine fibers. One setup for electrospinning can consist of a spinneret with a metallic needle, a syringe pump, a high-voltage power supply, and a grounded collector. A polymer, sol-gel, composite solution (or melt) can be loaded into the syringe and this liquid then driven to the needle tip by a syringe pump, forming a droplet at the tip. When a voltage is applied to the needle, the droplet can be first stretched into a structure called the Taylor cone. If the viscosity of the material is sufficiently high, varicose breakup does not occur (if it does, droplets are electrosprayed) and an electrified liquid jet is formed. The jet is can then be elongated and whipped continuously by electrostatic repulsion until it is deposited on the grounded collector. Whipping due to a bending instability in the electrified jet and concomitant evaporation of solvent (and, in some cases reaction of the materials in the jet with the environment) can allow this jet to be stretched to nanometer-scale diameters. The elongation by bending instability can result in the fabrication of uniform fibers with nanometer-scale diameters.

The therapeutic delivery system can also include a therapeutic guest agent, such as paclitaxel that can reversibly complex with the host molecules. It will be appreciated that the therapeutic guest agent can be dispersed on or within the particles before, during, or after electrospinning.

After forming the particles, a therapeutically effective amount of the particles can be implanted in a tissue of the subject. For example, a therapeutically effective amount of the particles can be injected into the subject at a target site tissue site. Where the target tissue site is a pulmonary tumor, for example, the tumoral target site can comprise the tissue of the pulmonary tumor itself. In this case, a therapeutically effective amount of the particles can be directly implanted at the tumoral target site via an intratumoral injection. It should be appreciated that the particles can be implanted in the subject via other suitable routes and using other suitable methods as well, such as intravenous, subcutaneous, intraperitoneal, transdermal, oral, and minimally invasive surgical routes.

It should also be appreciated that the particles can be administered to the subject without a carrier or, alternatively, as part of a pharmaceutically acceptable composition. The phrase "pharmaceutically acceptable" should be understood to mean a material (i.e., a nanoparticle) which is not biologically or otherwise undesirable, i.e., the material may be incorporated into a pharmaceutical composition administered to a subject without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug Administration.

Using a syringe or other similar device, the particles can be directly injected into the tissue site of the subject. Where the target tissue is a tumor, upon injection into the tumor, the particles can selectively accumulate in the tumor tissue due to the high permeability of the tumor vasculature. As the tumor develops, the permeability of the tumor can decrease and thereby cause the particles to remain embedded in the tumor tissue. Accumulation of the particles in the tumor tissue can be monitored by CT scan where, for example, the particles include an imaging agent. Once the particles have been dispersed in the tumor tissue, the therapeutic guest agent (e.g., paclitaxel molecules) can begin to dissociate from the host molecules via molecular affinity interactions (i.e., association/disassociation kinetics) at an affinity release rate that is faster than the degradation rate of the therapeutic guest agent (e.g., paclitaxel molecules).

By way of example, based on previously calculated dissociation rates of paclitaxel from CD molecules and/or by monitoring tumor size (i.e., tumor regression), a desired amount of paclitaxel can be delivered to the tumor tissue. Either before, simultaneous with, or after release of paclitaxel molecules from the CD molecules, additional paclitaxel molecules can be delivered to the emptied CD molecules. A subsequent intratumoral injection of paclitaxel into the tumor tissue may be performed to "re-fill" the emptied CD molecules. Alternatively, a subsequent intravenous injection and/or oral administration of paclitaxel can be injected into the subject to "re-fill" the emptied CD molecules. Tumor size can again be assessed, and periodic doses of paclitaxel continued until the tumor has partially or entirely regressed. By administering particles capable of reversibly complexing with paclitaxel, paclitaxel (or any other therapeutic guest agent) can be localized to the tumor tissue and thereby avoid the unwanted side effects often associated with repeated systemic drug administration.

In another example of the present invention, the therapeutic agent delivery platform can comprise an antibiotic-filled bandage that can be applied to a wound of a subject (e.g., following a surgical procedure). To prepare the bandage according to the present invention, at least one host molecule, such as a CD molecule can be complexed with at least one surface of a polymer that can then be applied to the bandage. As described above, CD molecules can be made suitable for coupling to at least one surface of a polymer by converting one of the hydroxyl groups of the CD molecules to a thiol group. The thiol-modified CD molecules can then be conjugated to bulk pEVOH using a bifunctional crosslinker, such as PMPI. The pEVOH/thiol-modified CD molecule mixture can then be mixed with a therapeutic agent, such as vancomycin and electrospun into nanofiber meshes (as described above). The nanofiber meshes can then be electrosprayed onto at least one surface of the bandage.

The bandage may then be placed on or around the surgical wound of the subject. Once the bandage has been securely positioned on or around the wound, the vancomycin molecules can begin to dissociate from the CD molecules via molecular affinity (i.e., association/dissociation kinetics) and permeate into and/or around the surgical wound. The vancomycin molecules can kill any bacteria present at the wound and/or prevent future bacterial infections at the wound site.

Based on previously calculated diffusion rates of vancomycin from CD molecules and/or by monitoring the wound site for infection and/or healing, an amount of vancomycin can be delivered to the bandage as needed. Either before, simultaneous with, or after release of vancomycin molecules from the CD molecules, additional vancomycin can be delivered to the emptied CD molecules. For example, a subsequent topical administration of vancomycin directly onto the bandage may be done to "re-fill" the emptied CD molecules. The wound site can again be assessed, and periodic doses of vancomycin continued until the wound site has partially or entirely healed. By providing the above-described bandage to the wound site, repeated changing of wound dressings can be avoided or minimized by periodically dosing the bandage with vancomycin.

In another example of the present invention may comprise coating implants such as, but not limited to, orthopedic implants with a therapeutic delivery platform. The therapeutic delivery platform may be a gel based platform. The therapeutic delivery platform uses a CD-based delivery system to deliver antibiotics at a desired rate. Unlike previous antibiotic coatings, the CD-based therapeutic delivery platform may be thinner than previous coatings and still deliver a therapeutic guest agent such as, but not limited to, antibiotics for a much longer duration than previous coatings. The therapeutic delivery platform may deliver a therapeutic guest agent such as, but not limited to, antibiotics for more than a month. The thinness of the therapeutic delivery platform is thin enough to not interfere with the fixation of orthopedic implants such as, but not limited to, pins, screws, K-wires, and external fixation pins. This specific example provides the ability to prevent early infection, at least 1 month, of any orthopedic implant and may be able to prevent infection for much longer periods of time. The therapeutic delivery platform may be modified to increase stiffness to better enable the coating of the therapeutic guest platform on the orthopedic implant.

A specific example of a therapeutic delivery platform that may be used in the above example are CD and dextrose-based polymers that are synthesized with lysine triisocynate acting as the crosslinker. The polymer stiffness can easily be adjusted by adjusting crosslinker ratio. Polymers are in situ polymerized onto the fixation pins, or any desired orthopedic implant. Even though polymerization occurs rapidly, under upon heating, under about 10 minutes, the reaction is allowed to proceed for about 45 minutes. An antibiotic such as, but not limited to, novobiocin is then loaded into the crosslinked polymer disks using a solvent/solution absorption method. Novobiocin may be prepared in dimethylformamide. The antibiotic may be loaded into the coated pins by incubating the samples in the solvent at room temperature for about 4 days. The antibiotic loaded pins are then vacuum dried at room temperature.

In another example the present invention may be used to slowly deliver a therapeutic guest agent such as, but not limited to, anti-inflammatory drugs and steroids to treat joint pain, arthritis, lower back pain, and similar types of ailments. In the present example the therapeutic delivery platform may be modified to have a low stiffness to enable the therapeutic delivery platform to be in a gel form. The therapeutic guest agents may be placed within the host molecules such as, but not limited to, CD and then may be placed within viscous gels which enables the therapeutic delivery platform to be injected into the desired location such as, but not limited to, joint space. The present invention allows for sustained therapy with less frequent injections because of the slow release of the therapeutic agent.

It will be appreciated that the present invention may find application to any number of other diseases or disease conditions other than those described above. For example, the present invention may have utility in treating infectious diseases, autoimmune diseases, cancers, vaccinating against various diseases, intraocular diseases, and gene delivery/gene therapy.

Other examples of diseases or conditions treatable by the present invention can include, but are not limited to, cardiovascular diseases, e.g., atherosclerosis, coronary artery disease, hypertension, hyperlipidemia, cardiomyopathy, volume retention; neurodegenerative diseases, e.g., Alzheimer's disease, Pick's disease, dementia, delirium, Parkinson's disease, amyotrophic lateral sclerosis; neuroinflammatory diseases, e.g., viral meningitis, viral encephalitis, fungal meningitis, fungal encephalitis, multiple sclerosis, charcot joint; myasthenia gravis; orthopedic diseases, e.g., osteoarthritis, inflammatory arthritis, reflex sympathetic dystrophy, Paget's disease, osteoporosis; lymphoproliferative diseases, e.g., lymphoma, lymphoproliferative disease, Hodgkin's disease; autoimmune diseases, e.g., Graves disease, hashimoto's, takayasu's disease, kawasaki's diseases, arthritis, scleroderma, CREST syndrome, allergies, dermatitis, Henoch-schlonlein purpura, goodpasture syndrome, autoimmune thyroiditis, myasthenia gravis, Reiter's disease, lupus, rheumatoid arthritis; inflammatory and infectious diseases, e.g., sepsis, viral and fungal infections, wound healing, tuberculosis, infection, human immunodeficiency virus; pulmonary diseases, e.g., tachypnea, fibrotic diseases such as cystic fibrosis, interstitial lung disease, desquamative interstitial pneumonitis, non-specific interstitial pneumonitis, lymphocytic interstitial pneumonitis, usual interstitial pneumonitis, idiopathic pulmonary fibrosis; transplant related side effects such as rejection, transplant-related tachycardia, renal failure, typhlitis; transplant related bowel dysmotility, transplant-related hyperreninemia; sleep disorders, e.g., insomnia, obstructive sleep apnea, central sleep apnea; gastrointestinal disorders, e.g., hepatitis, xerostomia, bowel dysmotility, peptic ulcer disease, constipation, post-operative bowel dysmotility; inflammatory bowel disease; endocrine disorders, e.g., hypothyroidism, hyperglycemia, diabetes, obesity, syndrome X; cardiac rhythm disorders, e.g., sick sinus syndrome, bradycardia, tachycardia, QT interval prolongation arrhythmias, atrial arrhythmias, ventricular arrhythmias; genitourinary disorders, e.g., bladder dysfunction, renal failure, hyperreninemia, hepatorenal syndrome, renal tubular acidosis, erectile dysfunction; cancer; fibrosis; skin disorders, e.g., wrinkles, cutaneous vasculitis, psoriasis; aging associated diseases and conditions, e.g., shy dragers, multi-system atrophy, osteoporosis, age related inflammation conditions, degenerative disorders; autonomic dysregulation diseases; e.g., headaches, concussions, post-concussive syndrome, coronary syndromes, coronary vasospasm; neurocardiogenic syncope; neurologic diseases such as epilepsy, seizures, stress, bipolar disorder, migraines and chronic headaches; conditions related to pregnancy such as amniotic fluid embolism, pregnancy-related arrhythmias, fetal stress, fetal hypoxia, eclampsia, preeclampsia; conditions that cause hypoxia, hypercarbia, hypercapnia, acidosis, acidemia, such as chronic obstructive lung disease, emphysema, cardiogenic pulmonary edema, non-cardiogenic pulmonary edema, neurogenic edema, pleural effusion, adult respiratory distress syndrome, pulmonary-renal syndromes, interstitial lung diseases, pulmonary fibrosis, and any other chronic lung disease; sudden death syndromes, e.g., sudden infant death syndrome, sudden adult death syndrome; vascular disorders, e.g., acute pulmonary embolism, chronic pulmonary embolism, deep venous thrombosis, venous thrombosis, arterial thrombosis, coagulopathy, aortic dissection, aortic aneurysm, arterial aneurysm, myocardial infarction, coronary vasospasm, cerebral vasospasm, mesenteric ischemia, arterial vasospasm, malignant hypertension; primary and secondary pulmonary hypertension, reperfusion syndrome, ischemia, cerebral vascular accident, cerebral vascular accident and transient ischemic attacks; pediatric diseases such as respiratory distress syndrome; bronchopulmonary dysplasia; Hirschprung disease; congenital megacolon, aganglionosis; ocular diseases such as glaucoma; and the like.

The following examples are for the purpose of illustration only and are not intended to limit the scope of the claims, which are appended hereto.

Example 1 Attaching Cyclodextrin to Surfaces and Showing Presence of Incorporated Drug Methods
CD-Thiol (CD-SH) Synthesis Cyclodextrin is made suitable for conjugation to a surface by converting one of the hydroxyl groups to a thiol. This is done using a modified protocol as follows: Mix 0.300 g of 6-Tosyl-β-CD and 0.300 g of thiourea (1:16.5 molar ratio) in a 50 ml round bottom flask. Add 15 ml of 80% Methanol. Heat mixture under reflux for 2 days at about 100° C. Evaporate mixture in vacuum. Add 4.5 ml of 100% methanol and reflux for 1 hr. Filter the solid and dissolve it in 10.35 ml of 10% NaOH at 50° C. for 5 hr. Adjust the pH of solution to 2 using 10% HCl. Add 0.750 ml of Trichloroethylene and stir solution overnight. Filter the resulting precipitate and wash it with water. Evaporate in vacuum followed by repeated recrystallization from water. Yield of CD-SH should be approximately 50% as calculated by NMR.

CD Conjugation to pEVOH

Cyclodextrin is then conjugated to bulk poly(ethylene co vinyl alcohol) using the bifunctional cross linker PMPI. This procedure is done as follows: Approximately 0.750 g of EVOH is dissolved in 14 ml of DMSO. 50 mg (0.23 mmol) of PMPI is then dissolved in 1 ml of DMSO. This solution of PMPI in DMSO is then added to the polymer melt. The solution reacts for 3 hours at room temperature under constant stirring.

Approximately 12.5 mg (0.024 mmol) of CD-SH is dissolved in 1.25 ml of 0.1 M NaOH (in DMSO) and incubated at room temperature for approximately 15 minutes. 17.5 µl of 6 M HCl is then added in order to neutralize the solution. The solution is then buffered with 0.25 ml of 0.5 M sodium phosphate. The pH of the solution is then adjusted to approximately 7 using 6 M HCl.

10 ml of the EVOH-PMPI solution in DMSO is then removed and placed in a glass vial. The activated CD-SH is then added to the remaining 5 ml of EVOH-PMPI solution in DMSO. The solution reacts for 8 hours at room temperature and under constant stirring. Conjugation is verified by NMR analysis, and conjugation efficiency by FTIR. The final product results in a 2.5% conjugation ratio (2.5% of all alcohol groups are conjugated with CD-SH).

CD-SH and pEVOH CD-SH Composition Analysis by NMR

Samples are dissolved 1 mg/ml in 1 ml deuterated chloroform, placed in RD-11 quartz glass sample tubes and run on a BRUKER 300 Mhz NMR looking for characteristic peaks at 2.4-3.0 ppm for EVOH and 3.3-4.1 ppm for CD.

FTIR Analysis of pEVOH Conjugation

Conjugation efficiency can be estimated by comparing infrared absorption peaks for EVOH at 3300 and CD-SH at 1573 $cm^{-1}$. This is done as follows: a solution of 1% pEVOH/CD-SH is made in 70% isopropanol and refluxed for 1 hr. This is then added to the liquid chamber of a horizontal attenuated total reflection-Fourier Transform infrared spectrometer using a Germanium single bounce crystal. Samples of unconjugated known CD-SH amounts are also prepared to create a calibration curve. Ideally loading is kept at 10% and below. This is typically the maximum loading amount for drug delivery devices, since further loading would result in destabilization of the device leading to large porous areas within the substructure.

Attachment to Gold Substrates

Cyclodextrin (CD) was modified to contain at least one thiol (—SH) group per ring. This CD-SH spontaneously associated with gold surface made by sputter coating surface with 100 Å gold. A chemically bound monolayer of CD-SH was detected using Attenuated Total Reflection-Fourier Transformation Infrared Spectroscopy (ATR-FTIR) on gold surfaces which had been extensively washed (FIGS. 1A-B).

Attachment to Polymer Substrates

As a model polymer substrate, we used poly(ethylene covinyl alcohol) (pEVOH) due to the availability of a reactive hydroxyl. 2D surfaces are made by either solvent casting or formation of an interpenetrating network (IPN) with tissue culture polystyrene surfaces. 3D surfaces are made by either electrospinning into nanofiber meshes or by solvent or particulate leaching from a solid mold.

pEVOH is conjugated with CD pockets by either conjugation using a bifunctional crosslinker or by direct conjugation. Using a bifunctional crosslinker such as PMPI, the polymer can first be pre-conjugated, where the isocyanate in PMPI is bound to hydroxyls on the pEVOH. Then, following surface fabrication, the free maleimide on PMPI can be reacted with CD-SH from above. This allows selective attachment on a polymer surface rather than throughout the polymer. Complete modification of the entire polymer can also be performed prior to surface fabrication if desired.

Using direct conjugation, tosyl chloride was reacted to the hydroxyls in pEVOH. Then, CD-amine was bound to the polymer by displacing the tosyl group. Surfaces manufactured using these polymers were similarly examined for cell attachment as the gold surfaces.

Drug Delivery from Surfaces

Figure 2:
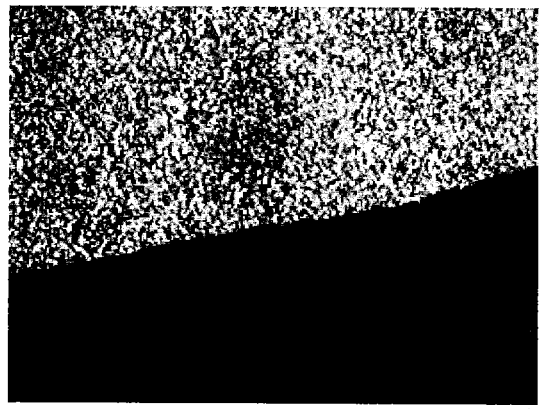
FIG. 2 is an image showing doxorubicin loaded select pockets of a CD-grafted pEVOH polymer surface. The image was taken at 20× magnification using 555 nm excitation and 576 nm emission filters.
Figure 3:
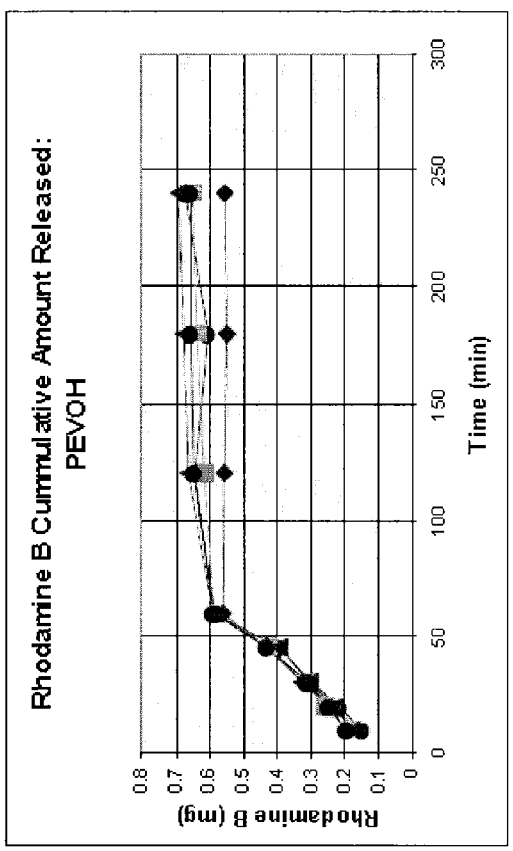
FIGS. 3A-B are graphs showing model drug release from CD-modified pEVOH. Tablets pressed from either pEVOH 9 (FIG. 3A) or CD-modified pEVOH (FIG. 3B) were mixed with the hydrophobic drug rhodamine in dry powder form. Polymer and drug were pressed into 3 mm pellets and cumulative release was examined over a period of several days (N=5); Release from the polymer with no CD shows a typical two phase diffusion release. With CD modification this two phase release is slowed substantially and much more linear.
Figure 3:
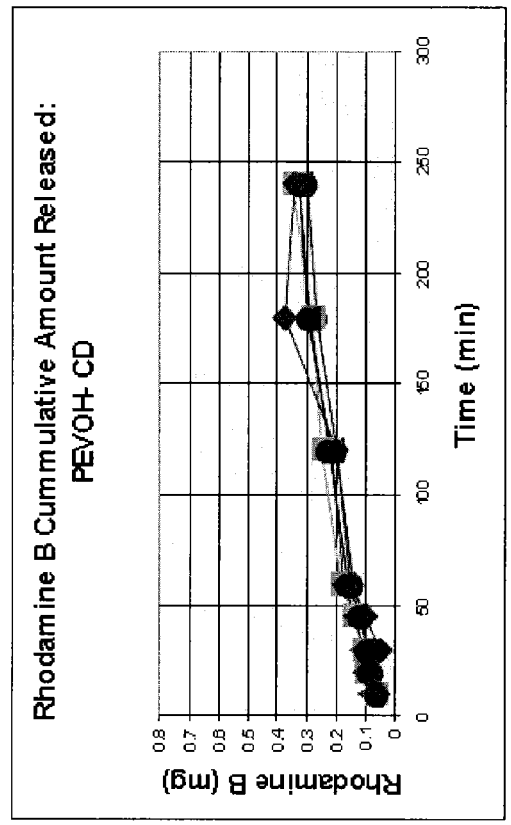
Figure 4:
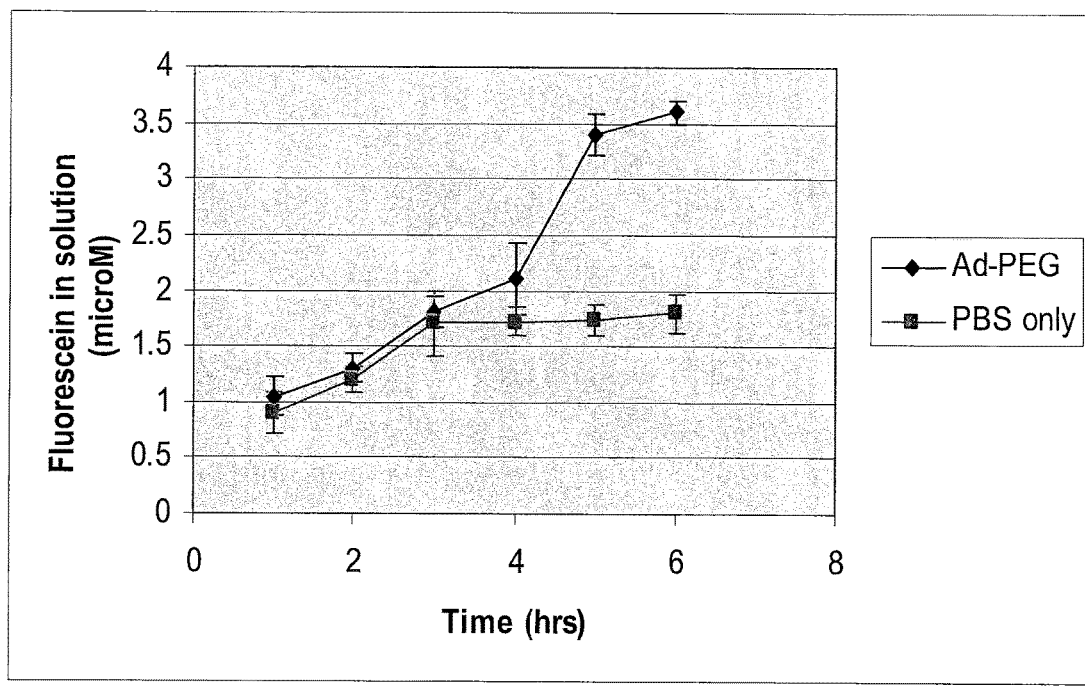
FIG. 4 is a graph representing the release of Ad-PEG3400-SAMSA fluorescein from a material (diamonds), and the displacement by Ad-PEG2000 (squares): Fluorescein released in solution under steady state in PBS, and shows affinity-based slow release: Upon the administration of a dummy (non-fluorescent) molecule to the material, some of the fluorescent molecules ("drug") is displaced, resulting in an intentional burst phase of release, also demonstrating the capacity of one molecule in the material to be replaced with another.

Polymer surfaces manufactured as above were examined for their capacity to bind and release drug. Drugs examined were either small hydrophobic drugs, such as doxorubicin (FIG. 2), or Ad-modified drugs (Ad-PEG-fluorescein (FIG. 4). The idea was that either hydrophobic molecules or molecule with conjugated hydrophobic tails would be released from a CD substrate based solely on association/dissociation kinetics, which is an entirely new paradigm in drug delivery, different from traditional mechanisms such as diffusion, polymer degradation, or external stimulus.

Drug in these substrates was demonstrated to be capable of moving from one CD pocket to another in a "sticky tape" fashion. Drug bound to a substrate was demonstrated to be capable of being knocked out by incubation with another hydrophobic molecule (bare Ad) (FIG. 4).

Results and Discussion

From this research, we have demonstrated the capability of using reversible interactions to load small biomolecules such as proteins onto a surface. These biomolecules can maintain their chemical and biological functions. The reversible attachment allows unique spatial and temporal arrangements of these molecules to be made and changed over time. In addition, high affinity interactions between the reactive subunits allows for molecular homing of a modified drug to the modified surface.

Example 2 Small Hydrophobic Drug Release from CD

Drugs Loaded into CD-Modified Polymer Surfaces
Materials

A β-cyclodextrin-Epichlorohydrin copolymer (50 mol % CD; 2-15 kDa) was purchased from CTD, Inc. (High Springs, Fla.). Poly(acrylic acid) (pAAc; 10 kDa; 40 wt % aqueous solution) was procured from Polysciences, Inc. (Warrington, Pa.). Desmodur RE (27 wt % triphenylmethane-4,4',4"-triisocyanate in ethyl acetate) was obtained from Bayer MaterialScience LLC (Pittsburgh, Pa.). 1-Adamantanemethylamine (Ad) and N-hydroxysuccinimide (NHS) were purchased from Acros Organics (Geel, Belgium) and used as received. 6-Amino β-cyclodextrin (CD; Supelco) and N,N'-dicyclohexylcarbodiimide (DCC) were obtained from Sigma-Aldrich (St. Louis, Mo.). SCM-mPEG$_{5000}$ and SCM-PEG$_{3400}$-Fluorescein were purchased from Laysan Bio, Inc. (Arab, Ala.). 1-Ethyl-3-[3-dimethylaminopropyl] carbodiimide Hydrochloride (EDC) was obtained from Pierce Biotechnology (Rockford, Ill.). Lissamine Rhodamine B ethylenediamine (LRB-EDA) was purchased from AnaSpec (San Jose, Calif.). Methylene chloride and chloroform were procured from Fisher Scientific (Pittsburgh, Pa.) and used as received. N,N'-dimethylformamide (DMF) and N-methylpyrrolidone (NMP) were obtained from Applied Biosystems (Foster City, Calif.). All reagents and solvents were of analytical grade and, unless noted otherwise, were used as received.

Synthesis and Characterization of Adamantane Derivatives
Monovalent Synthesis: Ad-PEG$_{3400}$-Fluorescein and Ad-mPEG$_{5000}$ Monovalent Ad derivatives were synthesized using 1-Adamantanemethylamine and either a methoxy PEG or a fluorescently-labeled PEG molecule terminated with an amine-reactive succinimidyl carboxymethyl (SCM) ester (SCM-mPEG$_{5000}$ or SCM-PEG$_{3400}$-Fluorescein, respectively). The coupling reactions were carried out in an organic solvent (methylene chloride) in order to solubilize the Ad groups and prevent hydrolysis of the succinimidyl ester. In a typical reaction, 21.2 µl (0.12 mmol) of 1-Adamantanemethylamine was dissolved in 4 ml of methylene chloride under vigorous stirring at room temperature. Then, 100 mg (0.024 mmol) of SCM-PEG$_{3400}$-Fluorescein, separately dissolved in 1 ml of methylene chloride, was slowly added dropwise to the Ad solution under vigorous stirring. The solution was left stirring at room temperature for 24 hours, at which time 5 ml of Millipore water was added. The methylene chloride was then removed using a rotary evaporator. Unreacted Ad and N-hydroxysuccinimide (NHS) byproduct were removed via desalting using a PD-10 Sephadex G-25M column (Supelco; MWCO<5000). The desalted product was then lyophilized in order to obtain a dry powder, which was stored at −20° C. until use.

Example 3 Different Antibiotics in CD-Surfaces

Methods

Poly(ethylene-co-vinyl alcohol) (PEVOH) was modified to contain β-CD side chains by first conjugating the polymer with a tosylate and then allowing for spontaneous reaction with a β-CD monoamine. The resulting compounds were characterized by NMR and determined to have 2-10% CD substitution depending on the feed ratio. PEVOH and PEVOH-CD were pressed into 3 mm tablets containing 10% drug. Initial experiments were performed using Rhodamine as the model drug. Later experiments were performed using antibiotics (Rifampin, Novobiocin and Vancomycin). Samples were placed in PBS and kept agitated at 37° C. Periodic aliquots were removed and evaluated for drug content by fluorescence, or UV/Vis absorbance detection.

In vivo experiments were performed by implanting pellets similar to those above into the dorsal midline of C57Bl/6 mice. Two days following implantation 1×10$^6$ bacteria (either E. coli or Staph. epi.) were injected subcutaneously adjacent to the implant site. Seven days following implantation the devices were retrieved and any colonizing bacteria were plated on agar and counted to determine extent of bacteria killing. PEVOH and PEVOH-CD implants both loaded and non-loaded were compared to mice who received either no antibiotic, or antibiotic as a subcutaneous injection on day 1.

Results

Release of the model drug Rhodamine from unmodified PEVOH was observed to be very rapid with 60% being released within 1 hr. Release of Rhodamine from PEVOH-CD was observed to be more rapid, with 90% release being observed over several days (up to 30 days) depending on CD modification ratio.

Figure 7:
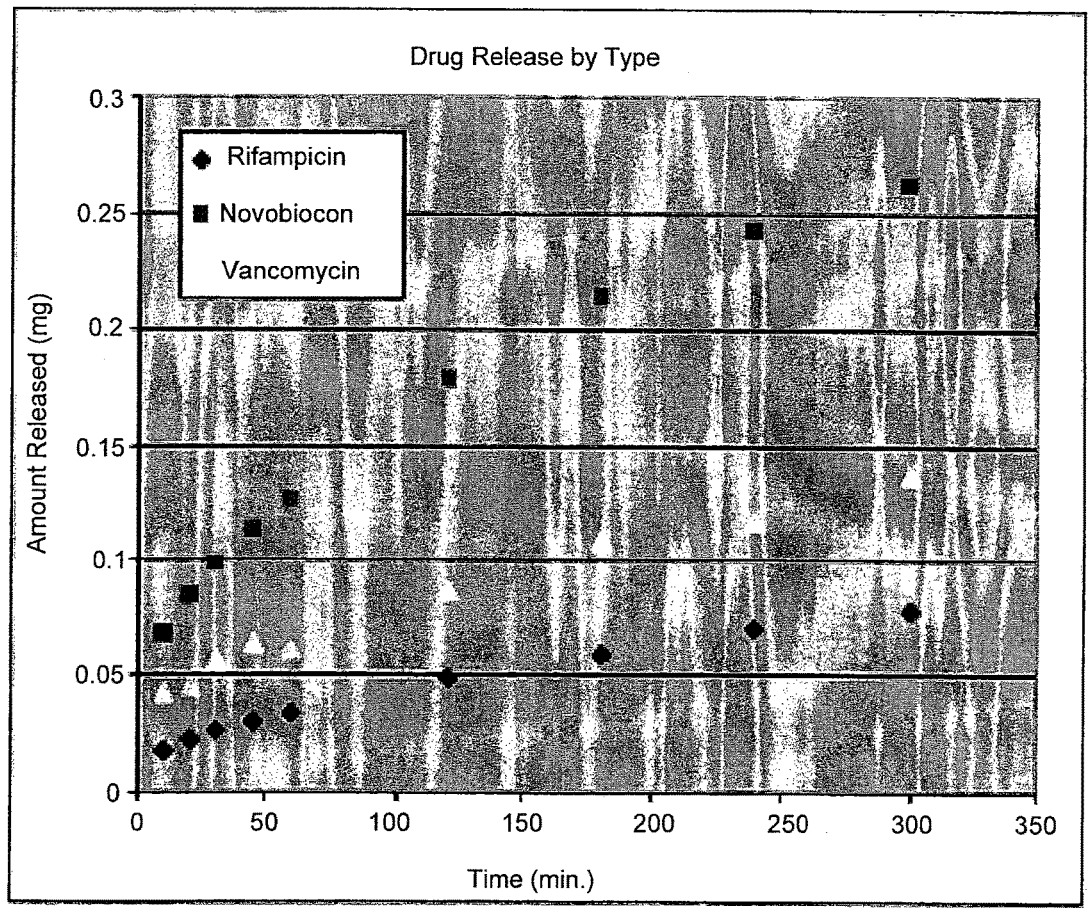
FIG. 7 is a plot showing the controlled release of antibiotics with varying size and hydrophobicity from CD-modified polymers (drugs are Novobiocin, Rifampin, and Vancomycin)

Antibiotics were observed to undergo similar release depending on the hydrophobicity and size of the drug. Novobiocin, the most hydrophilic underwent rapid non-linear release. Rifampin, the most hydrophobic underwent slower release. Vancomycin was observed to undergo a release rate between these two (FIG. 7).

Figure 8:
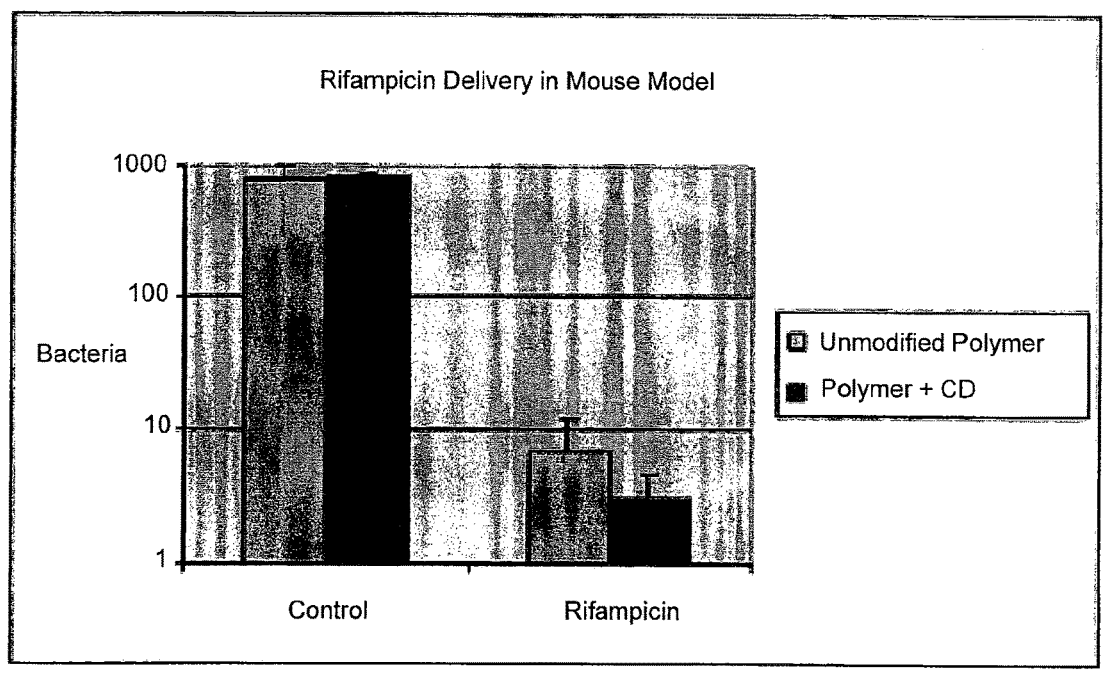
FIG. 8 is a plot demonstrating the controlled in vivo release of antibiotics and their ability to reduce a concurrent *E. coli* infection. (polymers are either unmodified (light) or CD-modified (dark))

Drug delivery pellets which were implanted subcutaneously showed extensive colonization if no antibiotic was included. In short term studies both the PEVOH and PEVOH-CD pellets had the capacity to kill local bacteria (FIG. 8).

Example 4 Different Number of Rifampin Arms Conjugated to Ad

Methods
In Vitro Release Studies 10 mg polymer-drug pellets (n=5) were placed in wells of a 24-well standard tissue culture plate in 1 ml of 1× phosphate buffered saline (PBS) at 37° C. The plate was protected from light and shaken at 200 revolutions per minute at 37° C. At each time point, 200 µl of PBS with dissolved drug was removed from each well and placed into a 96 well plate for later analysis. The removed liquid was replaced by 200 µl of fresh PBS kept at 37° C. for the duration of the study. Samples were analyzed using a Safire Microplate Reader (Tecan, Durham, N.C.) on absorbance mode, with measurement wavelength 474 nm and reference wavelength 650 nm.

Drug Loading

Unmodified rifampin (Fisher BioReagents, Pittsburgh, Pa.) was loaded at a 5% fraction of the total mass of the pellet. Drug was mixed with polymer in a microcentrifuge tube, dissolved in a small amount of water, mixed thoroughly, and dried in a vacuum oven. Polymer-drug pellets were pressed using 10 mg of polymer-drug mixture placed in a 3 mm die under 0.5 tons of pressure for 1 minute.

Formation and Analysis of Modified Rifampin (Ortho-pyridyl)disulfide-PEG-succinimide (OPSS-PEG-SCM) (MW 5000, LaysanBio, Arab, Ala.) was dissolved in HPLC grade anhydrous dichloromethane at room temperature for 10 minutes. Enough adamantane amine (Sigma-Aldrich) for a 1:5 Adamantane:PEG mass ratio was added to the OPSS-PEG-SCM solution and allowed to react for 4 hours at room temperature. Solvent was then evaporated and samples were resuspended in water and centrifuged for 15 minutes. The aqueous phase was transferred to a 3,500 MWCO dialysis cassette (Pierce, Rockford, Ill.) and dialyzed against 8 L of water for 1 day, changing the water at 1 hour and 4 hours. The solution was then lyophilized overnight to obtain dry Adamantane-PEG-OPSS. This product was dissolved in 2.5 ml water and 50 µl β-mercaptoethanol, a strong reducing agent. The reaction was allowed to continue until an absorbance peak appeared at 343 nm in the reaction mixture, indicating that the byproduct pyridyl-2-thione had formed (Guinn, A R et al., Georgia Institute of Technology Master's Thesis, 2006). The reaction mixture was dialyzed and lyophilized as before, and dry adamantane-PEG-thiol (Ad-PEG-SH) was obtained.

N-(p-Maleimidophenyl) isocyanate (PMPI) (Pierce, Rockford, Ill.) was reacted in DMSO with rifampin (Fisher BioReagents, Pittsburgh, Pa.) with a 2:1 molar excess of PMPI to rifampin hydroxyl groups (5 per molecule). The solution was allowed to react at room temperature for 4 hours. After reaction, the PMPI-rifampin solution was separated using a Sephadex G-25 desalting column (Sigma-Aldrich, St. Louis, Mo.). When two peaks were seen in the amount of solute leaving the column over time, only the flow-through before the end of the first peak was retained. Solvent was evaporated and the sample redissolved in a large volume of water (250 ml for 10-5 mol rifampin). Assuming 80% yield from the rifampin reaction to PMPI, Ad-PEG-SH obtained before was added to the rifampin-PMPI solution in water at 1:1, 2:1, and 4:1 ratios of Ad-PEG-SH to rifampin-PMPI. These solutions were allowed to react for 1 hour at room temperature to allow for the spontaneous reaction of the maleimide component of rifampin-PMPI to form a stable thioether linkage with the Ad-PEG, resulting in Ad-PEG-rifampin (Annunziato, M E et al., *Bioconjugate Chem.* 1993; 4: 212-218). The solution was lyophilized to obtain dry Ad-PEG-rifampin of 1:1, 2:1, and 4:1 molar ratios of PEG to rifampin. Samples of rifampin, (Ad-PEG)2-rifampin, Ad-PEG-OPSS, and 1-adamantanemethylamine were analyzed using NMR (CWRU Dept. of Macromolecular Science, Cleveland, Ohio).

Bacterial Killing Assays

10 µl of *staphylococcus epidermidis* (strain RP-62A) suspension was added to 5 ml tryptic soy broth (TSB) and shaken overnight at 37° C. 500 ml of the resulting suspension was added to 100 ml fresh TSB and shaken for 2 hours at 37° C. in order to restore the bacteria to exponential growth phase. 500 µl of the resulting suspension was added to centrifuge tubes containing 5 ml of various concentrations of rifampin or Ad-PEG-rifampin. Control groups consisted of a sample with no antibiotic added and a sample with no bacteria added to simulate complete killing. Sample turbidity (an indirect measure of bacterial proliferation) was measured using a Safire Microplate Reader (Tecan, Durham, N.C.) in absorbance mode, with measurement wavelength 500 nm and reference wavelength 920 nm.

Results
NMR Analysis of Modified Rifampin

Figure 5:
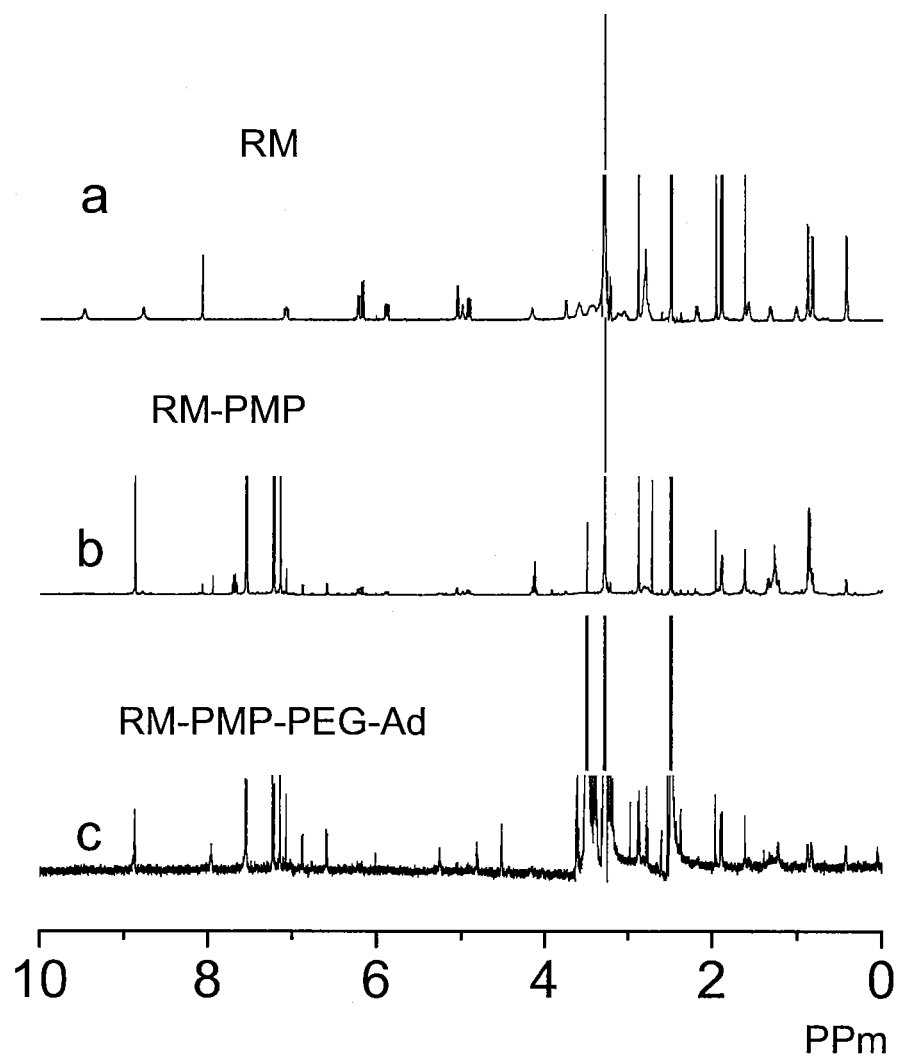
FIG. 5 is a series of $^1$H NMR of modified rifampin spectra showing the conjugation of additional PEG-Ad arms to Rifampin. Top panel: Rifampin; Middle panel: Addition of bi-functional crosslinker PMPI; Bottom panel: Adamantane-PEG1-rifampin following administration of 1:1 feed ratio of Adamantane and rifampin-PMP
Figure 18:
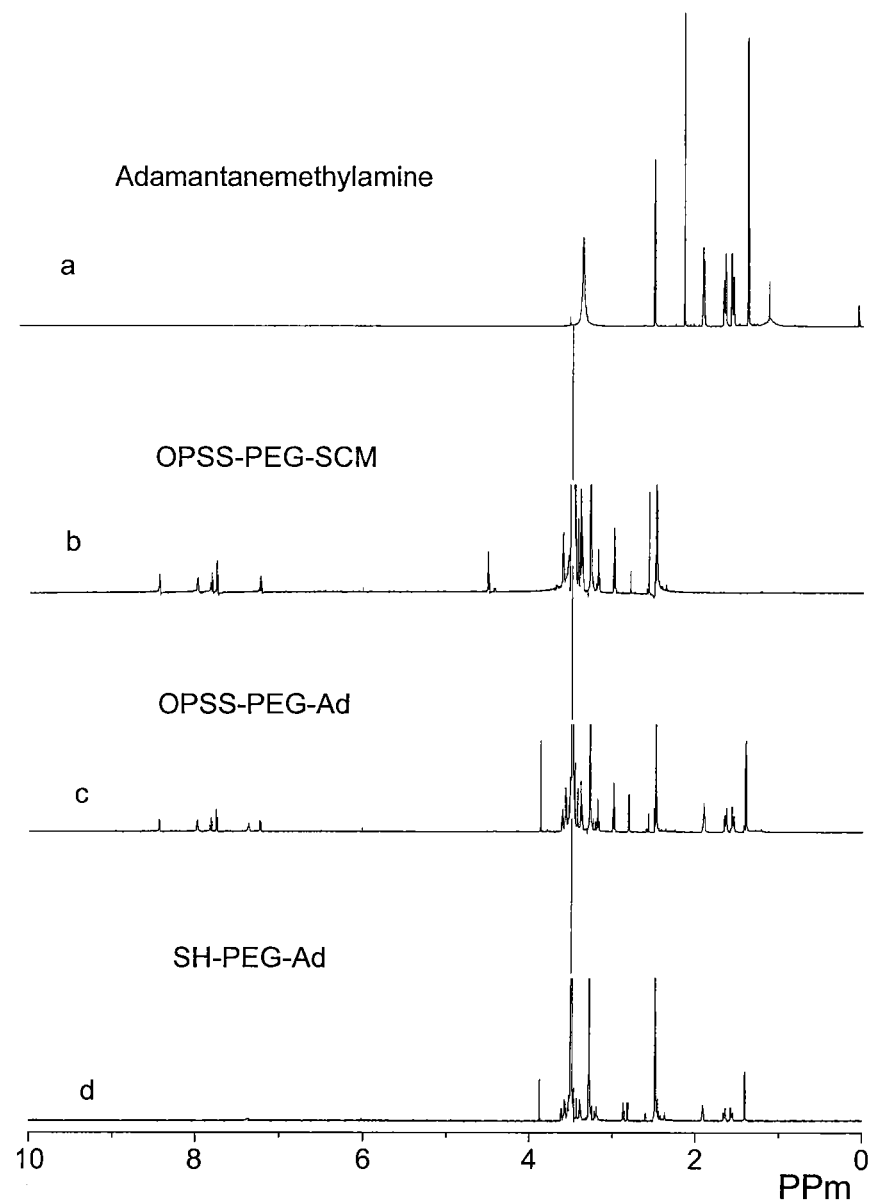
FIG. 18 is a series of partial NMR spectra showing modified Adamantane with PEG derivatives.

A large peak was found in all PEG-containing samples at about 3.67 ppm. In FIG. 5, regions of interest for the spectra for unmodified rifampin and the modified drug (Ad-PEG)2-rifampin are shown. Peaks as detected by graduate student Travis Sill are marked in blue. In FIG. 18, notable peaks for 1-adamantanemethylamine were at 1.42, 1.62, 1.69, 1.97, and 2.29 ppm.

Bacterial Killing Assays

Figure 6:
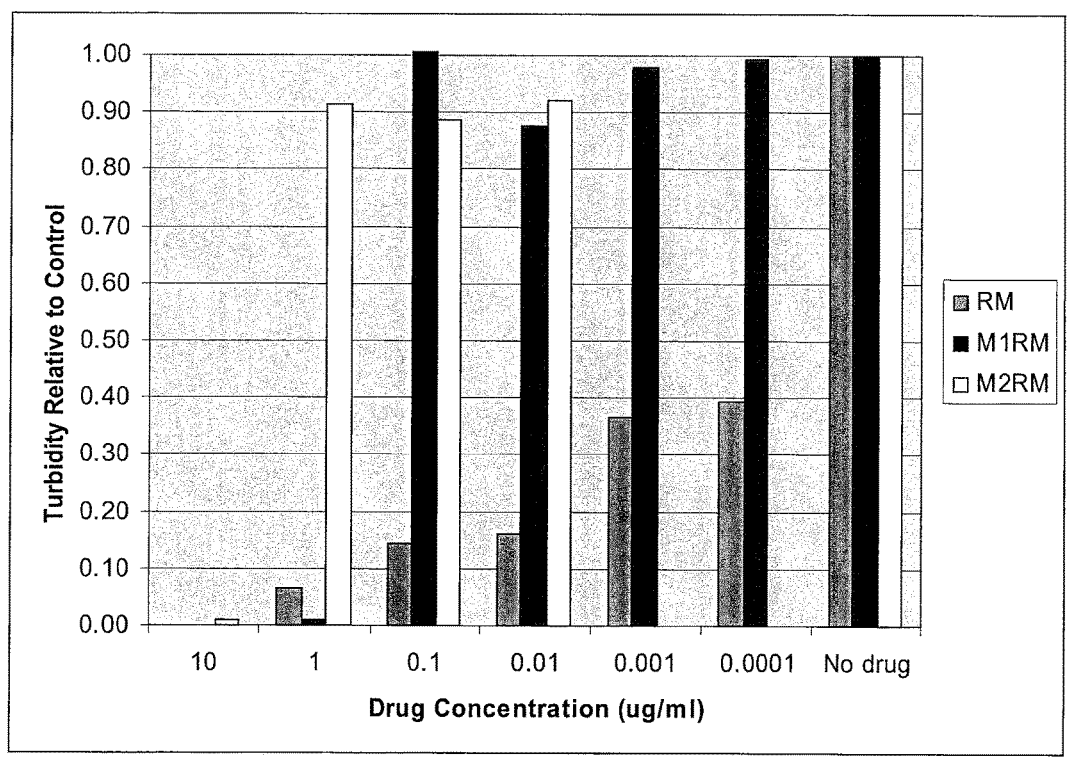
FIG. 6 shows the Bactericidal effect of unmodified rifampin (RM) or rifampin with one arm ($M_1RM$) or two arms ($M_2RM$) on *Staphylococcus epidermidis*, following non-specific arm conjugation.

The killing of unmodified and modified drug is shown in FIGS. 6A-B, respectively. The turbidity of a 5 ml liquid culture relative to controls is shown, where 100% corresponds to no drug and 0% (full killing) corresponds to no bacteria in the sample. This trial was only run once in order to make an order-of-magnitude assessment of the concentration of unmodified and modified drug required to kill.

Example 5 Drug Model Containing Varying Amounts of Adamantane Groups

Materials and Methods
Multivalent Synthesis: pAAc-Ad Derivatives

Multivalent pAAc-Ad derivatives with varying degrees of Ad content (1.5, 3, 4.5, and 6 mol %, corresponding to an average of 2, 4, 6, or 8 Ad groups per polymer chain) were prepared. In the following, the synthesis of pAAc-Ad-1.5 is described, where 1.5 refers to the mol % of Ad to AAc repeats in the feed ratio. The coupling of Ad with pAAc was carried out in an aprotic solvent (NMP) in the presence of N,N'-dicyclohexylcarbodiimide (DCC) according to a previously reported protocol. In a typical reaction, 1.042 ml of a 40 wt % aqueous pAAc solution was added to 14 ml of NMP. The water was then removed using a rotary evaporator, causing the pAAc (500 mg, 6.94 mmol of AAc repeat units) to precipitate. The pAAc was then dissolved under reflux at 70° C. over a period of 12 h, while undergoing vigorous stirring. 18.4 µl (0.10 mmol) of 1-Adamantanemethylamine and 42.9 mg (0.21 mmol) of DCC dissolved in 1 ml of NMP were then introduced successively into the pAAc solution under vigorous stirring. The temperature was maintained at 70° C. for 24 h. The system was allowed to cool to room temperature and the dicyclohexylurea byproduct was removed by filtration. The pAAc-Ad-1.5 product was subsequently precipitated in 30 ml of chloroform. The precipitate was pelleted via centrifuging at 4400 RPM for 10 minutes and the supernatant was removed. The product was resuspended in chloroform and the process was repeated. The pAAc-Ad-1.5 product was dried under vacuum to remove residual chloroform. The product was then dissolved in 10 ml of Millipore water and dialyzed extensively using a 7 kDa MWCO Slide-A-Lyzer dialysis cassette (Pierce Biotechnology). Following dialysis, the product was lyophilized to give a dry powder, which was stored at −20° C. until use.

35 mg of each pAAc-Ad derivative was subsequently labeled using Lissamine Rhodamine B ethylenediamine (LRB-EDA) for in vitro drug loading and release studies, where the fluorescent marker is serving as the model drug. Briefly, 35 mg (3.5 µmol) of the desired pAAc-Ad derivative was dissolved in 1.5 ml of Millipore water. 2.5 mg (3.5 µmol) of LRB-EDA and 1.5 mg (7.0 µmol) of EDC were each dissolved separately in 0.5 ml of Millipore water and were added to the aqueous pAAc-Ad solution dropwise. The reaction was carried out for 4 hours at room temperature under constant agitation. Unreacted LRB-EDA and EDC were removed via desalting using a PD-10 Sephadex G-25M column (Supelco; MWCO<5000). The desalted product was then lyophilized in order to obtain a dry powder, which was stored at −20° C. until use.

Characterization

Figure 9:
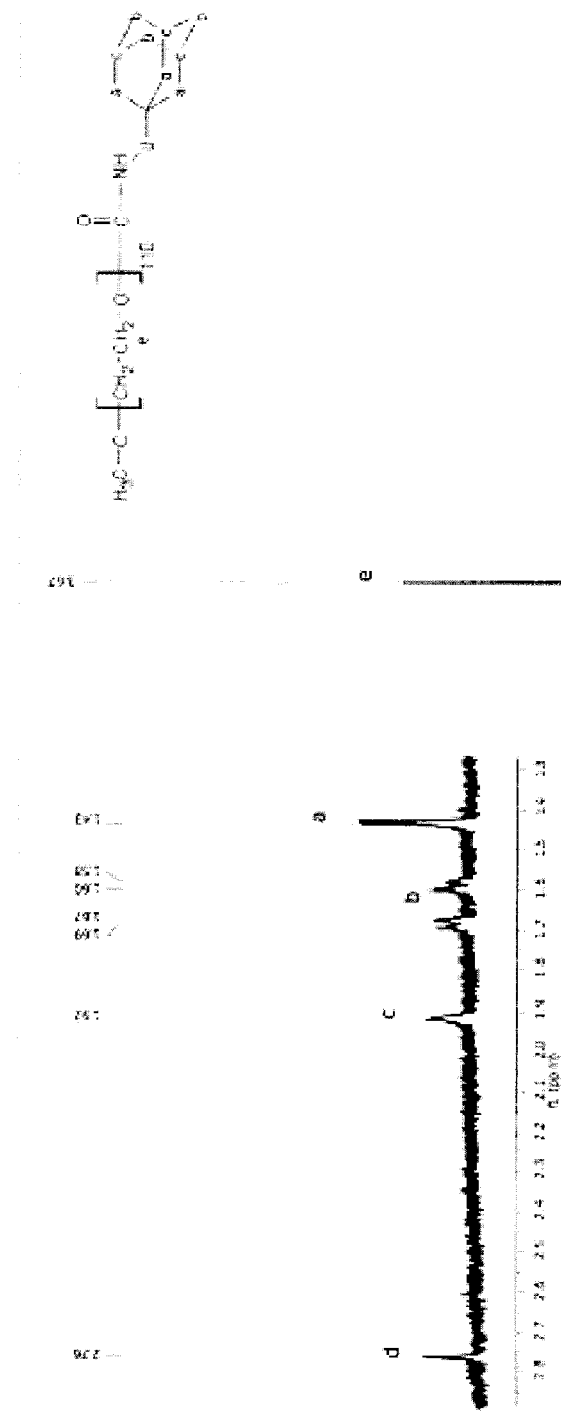
FIG. 9 is a $^1$H-NMR spectrum of Ad-mPEG$_{5000}$. $^1$H-NMR (600 MHz; D$_2$O): δ3.67 (t, 440H, PEG[CH$_2$CH$_2$O]$_{110}$, J=9.67 Hz); 2.76 (s, 2H, Ad[CCH$_2$NH]); 1.92 (s, 3H, Ad[CH$_2$CHCH$_2$]); 1.63 (dd, 6H, Ad[CHCH$_2$CH], J=56.3 Hz, 13.7 Hz); 1.43 (d, 6H, Ad[CHCH$_2$C], J=2.43 Hz)
Figure 9:

The $^1$H NMR spectra of the various Ad derivatives were recorded on a Varian Inova NMR spectrometer operating at a proton frequency of 600 MHz. (FIG. 9) All samples were prepared at a concentration of 10 mg ml$^{-1}$ in D$_2$O (Norell, Inc.; Landisville, N.J.). For the Ad-mPEG$_{5000}$ product the conjugation efficiency was determined by comparing the area under the Ad peak at 1.43 ppm (d, 6H, Ad[CHCH$_2$C], J=2.43 Hz) to the area under the PEG peak at 3.67 ppm (t, 440H, PEG[CH$_2$CH$_2$O]$_{110}$, J=9.67 Hz). For the Ad-PEG$_{3400}$-Fluorescein product as well as the various pAAc-Ad derivatives the spectra could not be analyzed quantitatively due to overlapping of peaks. The various pAAc-Ad derivatives were further analyzed using ATR-FTIR.

SPR Analysis

Surface plasmon resonance (SPR) spectroscopy is a technique used in a variety of biosensors in order to analyze molecular interactions in real-time. A number of commercially available products are produced by Biacore, including the Biacore X100 (GE Healthcare; Piscataway, N.J.), which was used in these studies. In a typical experiment, a ligand is immobilized on a carboxymethylated-dextran sensor chip, over which an aqueous solution carrying an analyte is passed. As the analyte binds to the immobilized ligand at the sensor surface, it causes an increase in the refractive index, which is then converted to resonance units (RUs) and plotted as a function of time. From this plot, information regarding the binding kinetics, affinity, and selectivity can be obtained.

Immobilization of 6-Amino β-Cyclodextrin was carried out internally within the biosensor system using a carboxymethylated-dextran sensor chip (CM5 research grade; Biacore). For this step, covalent immobilization was conducted at 25° C. using carbodiimide chemistry. In brief, the sensor surface was activated using a 1:1 (v:v) mixture of 0.4M EDC and 0.1M NHS. Following activation of the sensor surface, a solution of 6-Amino β-Cyclodextrin (50 µg ml$^{-1}$ in 10 mM sodium acetate, pH 5) was passed over the sensor chip at a flow rate of 10 µL min$^{-1}$ (contact times of 3 or 7 minutes were used in order to alter the immobilization levels). Unreacted sites were then blocked using a 1M ethanolamine solution (pH 8.5). The sensor chip was then washed extensively using running buffer (1×PBS, pH 7.4).

1 mM solutions of the various pAAc-Ad derivatives and a 7 mM solution of Ad-mPEG$_{5000}$ were then prepared in 1×PBS (pH 7.4) and filtered through 0.2 µm filters. Simple binding analyses were then conducted at 25° C. for each analyte. The analytes were passed over the sensor surface at a flow rate of 10 µL min$^{-1}$ for 1 minute. Following this association phase, running buffer was passed over the surface for a period of 2 minutes in order to cause dissociation of bound molecules. For multivalent systems this dissociation phase was followed by a subsequent regeneration step in which a 10 mM 6-Amino β-Cyclodextrin solution was passed over the sensor surface for a period of 1 minute. The measured response at various time points was recorded in order to obtain information regarding binding levels and the stability of the different interactions.

Immobilization

For immobilization of CD within the carboxymethylated-dextran matrix at the sensor chip surface, two different contact times (3 and 7 minutes) were utilized in order to alter the level of covalently bound host sites. These contact times led to immobilization levels of 45 and 245 RUs, respectively. It has been demonstrated empirically that a response of 100 RUs is equivalent to a ligand concentration of approximately 1 mg ml$^{-1}$ within the dextran matrix. Thus, the two immobilization levels correspond to average CD concentrations ($C_{avg}$) of approximately 0.45 mg ml$^{-1}$ (~0.4 mM) and 2.45 mg ml$^{-1}$ (~2.1 mM), respectively. In order to gain a better understanding of the interactions between the sensor chips containing different levels of immobilized CD molecules and the various mono- and multivalent Ad derivatives it is helpful to estimate the maximum effective concentration. An estimation for $C_{eff,max}$ can be obtained using equation 3

$$C_{eff,max} = \frac{n_H(L)}{\left(\frac{4}{3}\right)\pi N_{Av} L^3} \quad (3)$$

Where $n_H(L)$ is the number of accessible host sites in the probing volume defined by the linker length L, and $N_{Av}$ is Avogadro's number. For disordered host matrices, such as is found in the dextran matrix of the CM5 sensor chip, $C_{eff,max}$ can be estimated using the average number of accessible host sites in the probing volume, which gives equation 4:

$$C_{eff,max} = \frac{\left(\frac{4}{3}\right)\pi N_{Av} L^3 C_{avg} - 1}{\left(\frac{4}{3}\right)\pi N_{Av} L^3} \quad (4)$$

Dividing through by the denominator leads to equation 5:

$$C_{eff,max} = C_{avg} - \frac{1}{\left(\frac{4}{3}\right)\pi N_{Av} L^3} \quad (5)$$

Based on equation 5 it is clear that as the linker length, L, tends to infinity the maximum effective concentration approaches $C_{avg}$. The maximum effective concentration as a function of the linker length is depicted in FIG. 10 for the two $C_{avg}$ values calculated for the immobilization levels used in this study.

Figure 10:
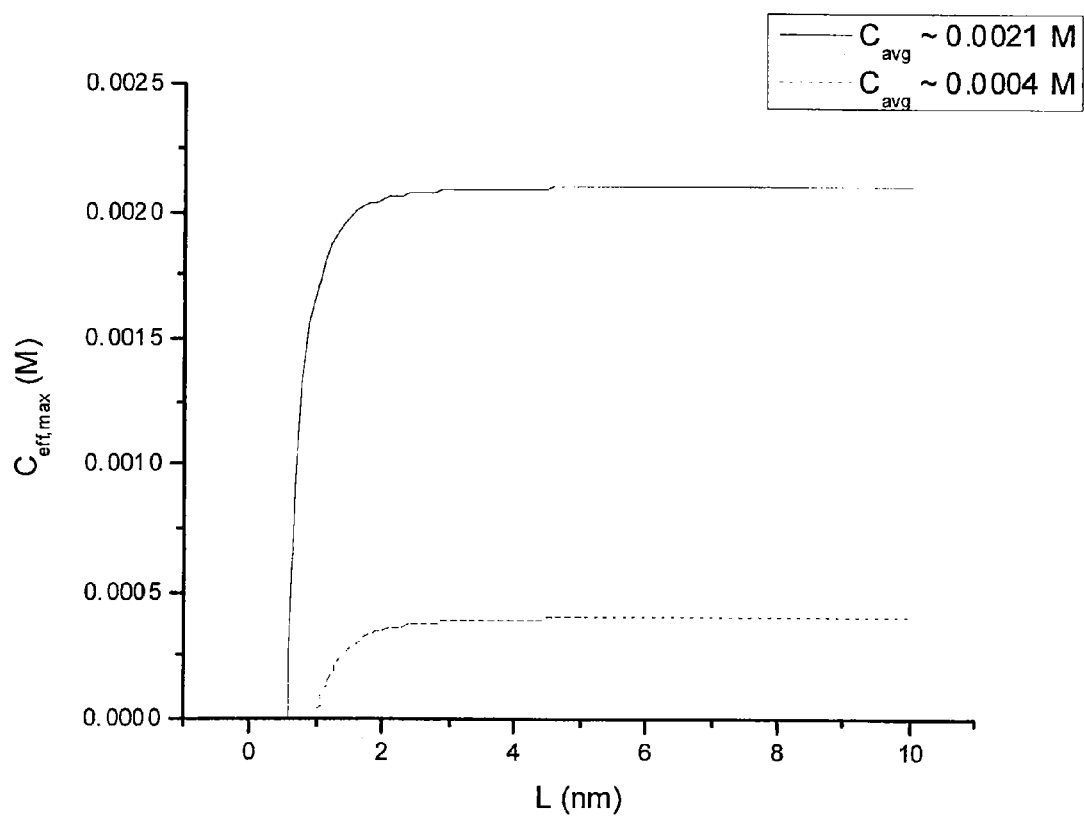
FIG. 10 is a plot comparing the dependence of $C_{eff,max}$ on the linker length (the space between multiple Adamantane groups), L.

As demonstrated in FIG. 10, for smaller values of $C_{avg}$, longer linker lengths are required in order to obtain a positive $C_{eff,max}$. For a $C_{avg}$ of approximately 2.1 mM, a linker length of only 0.57 nm is required to obtain a positive $C_{eff,max}$, as compared to a linker length of 1 nm for a $C_{avg}$ of approximately 0.4 mM. (Note: In practice, a linker length of at least 1.54 nm would be required in order to form a multivalent interaction, as the radius of the CD cavity is approximately 0.77 nm.). While this result is intuitive (the lower the concentration of host sites, the larger the probing volume must be in order to form a multivalent interaction) it has important implications for the design of a potential drug delivery device based on multivalent interactions. It is imperative that the concentration of host sites within the matrix is high enough for multivalent interactions to occur. Interestingly, as the number of guest molecules along the polymer backbone is increased, the linker length actually decreases. However, the probability of having two Ad groups spaced far apart actually increases. Thus, while the probability of forming at least a divalent interaction would increase, the probability of forming multivalent interactions of higher valency could actually decrease, unless the $C_{eff,max}$ is sufficiently high.

Binding and Stability Analyses

Figure 11:
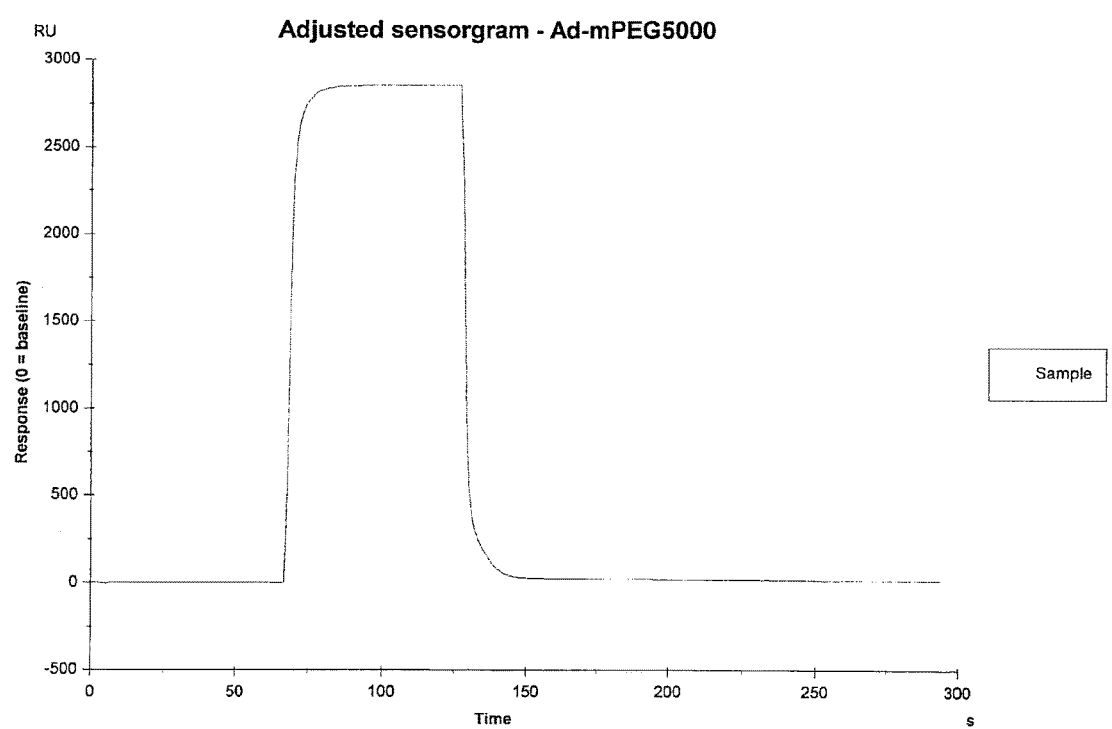
FIG. 11 is a sensorgram showing the interaction of a 7 mM aqueous Ad-mPEG$_{5000}$ solution with a CD-modified (45 RUs) sensor chip. The baseline was adjusted to 0 in order to demonstrate the magnitude of the binding response. A indicates injection of Ad-mPEG$_{5000}$ solution, while B indicates the beginning of the dissociation phase.

In order to analyze the interactions between a multivalent CD matrix and a variety of mono- and multivalent Ad derivatives, simple binding analyses were performed using a Biacore X100. All of the pAAc-Ad derivatives were prepared as 1 mM solutions in 1×PBS, pH 7.4, while Ad-mPEG$_{5000}$ was prepared at a concentration of 7 mM. All analyses were performed at 25° C. using a flow rate of 10 µL min$^{-1}$. As illustrated in FIG. 11, a positive response was observed after injection of an aqueous solution of Ad-mPEG$_{5000}$ (A), which indicates adsorption of the analyte to the CD-modified matrix.

The analyte was passed over the sensor chip surface for 60 seconds, after which the chip was washed with 1×PBS (B) in order to dissociate the bound Ad-mPEG$_{5000}$. From the sensorgram it is apparent that the Ad-mPEG$_{5000}$ derivative interacted positively with the CD-containing matrix. Additionally, both the association phase and the dissociation phase were relatively rapid, indicating that the kinetics of this interaction are fairly quick. Furthermore, the signal returned completely to baseline upon washing with 1×PBS. Thus, all of the bound Ad-mPEG$_{5000}$ was dissociated from the chip without the need for a competitive molecule. The fast kinetics and complete dissociation indicate that the interaction was occurring through a monovalent mechanism as was expected. Additionally, due to the rapid dissociation it appears that multivalent interactions may be required in order to substantially retard drug release.

Figure 12:
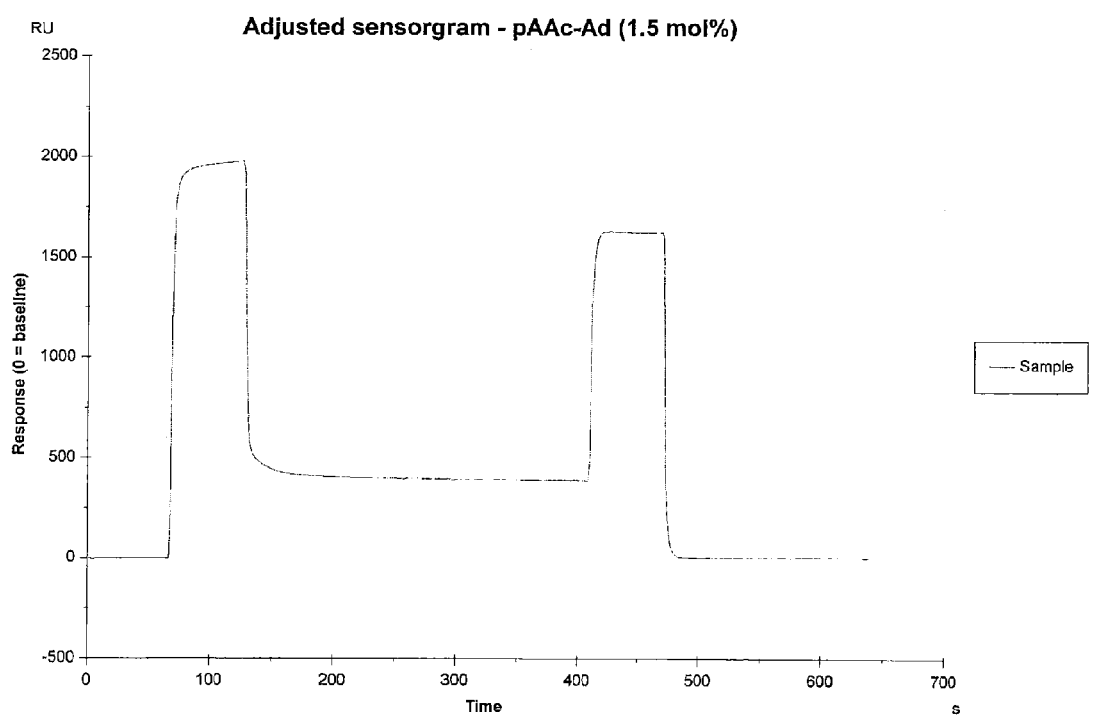
FIG. 12 is a sensorgram showing the interaction of a 1 mM aqueous pAAc-Ad-1.5 solution with a CD-modified (245 RUs) sensor chip. The baseline was adjusted to 0 in order to demonstrate the magnitude of the binding response. A indicates injection of pAAc-Ad-1.5 solution. B indicates the beginning of the dissociation phase. C indicates injection of a 10 mM aqueous CD solution for regeneration of the sensor chip. D indicates a washing step using 1×PBS.

A binding analysis with pAAc-Ad-1.5 also indicated a positive interaction between the Ad derivative and the CD-containing matrix (FIG. 12). However, for this interaction the signal did not return completely to baseline upon washing with 1×PBS, indicating that some of the pAAc-Ad-1.5 molecules were stably bound to the matrix.

Even after the extensive dissociation phase, the signal did not return completely to baseline. Thus, a 10 mM aqueous CD solution was passed over the matrix (C) in order to compete with the immobilized CD groups for the Ad guest molecules. This concentration (10 mM) is substantially higher than the maximum effective concentration for this matrix (2.1 mM). Thus, intramolecular binding will no longer dominate over intermolecular binding. As a result, uncomplexed guest molecules are more likely to form an intermolecular interaction with a free CD group in solution, which leads to dissociation of the bound pAAc-Ad-1.5 after washing with 1×PBS (D). Again, the association phase and the initial dissociation phase are relatively rapid. However, some molecules are stably bound and have a much slower dissociation rate, which indicates a much higher affinity for the CD matrix. This increased affinity and the fact that the signal did not return completely to baseline is indicative of a multivalent interaction. This conclusion is strengthened further by the regeneration of the surface using a 10 mM CD solution, which can easily be explained using multivalency and the principle of the effective concentration. However, not all of the pAAc-Ad-1.5 formed a stable interaction with the CD-containing matrix. It is probable that a portion of pAAc-Ad-1.5 molecules only contain one Ad group. These molecules would not be able to form a multivalent interaction and would thus be subject to the same rapid dissociation as was seen with the Ad-mPEG$_{5000}$ interaction. Additionally, it is possible that some pAAc-Ad-1.5 molecules are interacting nonspecifically with the dextran matrix. In order to correct for nonspecific interactions, the pAAc-Ad-1.5 solution was also passed over a reference surface consisting entirely of a carboxymethylated-dextran matrix (without CD). The response obtained at the reference surface was then subtracted from the response obtained at the CD-modified surface to give FIG. 13.

Figure 13:
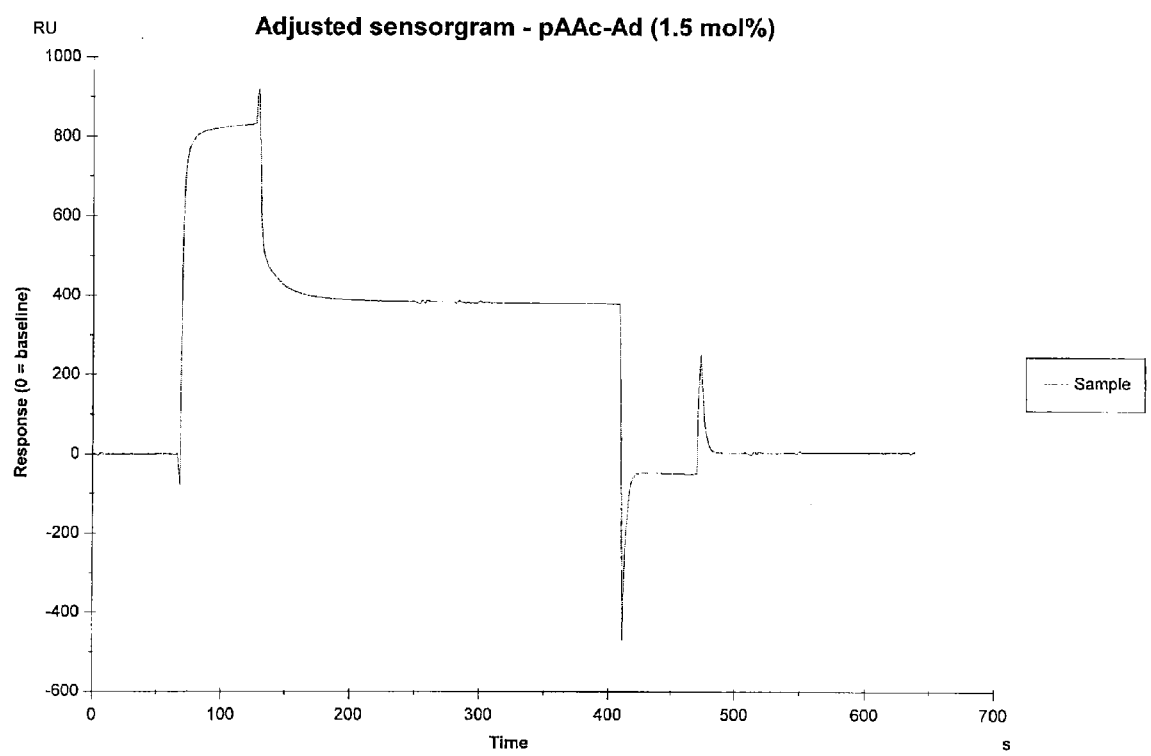
FIG. 13 is a reference-subtracted sensorgram for the interaction of a 1 mM aqueous pAAc-Ad-1.5 solution with a CD-modified (245 RUs) sensor chip. The baseline was adjusted to 0 in order to demonstrate the magnitude of the binding response. A indicates injection of pAAc-Ad-1.5 solution. B indicates the beginning of the dissociation phase. C indicates injection of a 10 mM aqueous CD solution for regeneration of the sensor chip. D indicates a washing step using 1×PBS.

Comparing FIGS. 12 and 13, it is evident that a fairly large amount of nonspecific binding did occur. However, of the molecules that did interact with the matrix in a specific manner, nearly 50% were bound stably after the dissociation phase. Again, this indicates that some interactions were occurring via a multivalent mechanism, but it also demonstrates that a substantial percentage of pAAc-Ad-1.5 molecules were unable to form multiple interactions. This may be due to the relatively low $C_{eff,max}$ within the matrix, which is two orders of magnitude smaller than values reported by Crespo-Biel et al. at a 2-dimensional surface. This argument is further strengthened by the fact that a very low percentage of pAAc-Ad-1.5 molecules were able to stably bind to the sensor chip containing the lower immobilization level of 45 RUs (Data not shown). Additionally, some of the response may still be due to nonspecific interactions.

Figure 14:
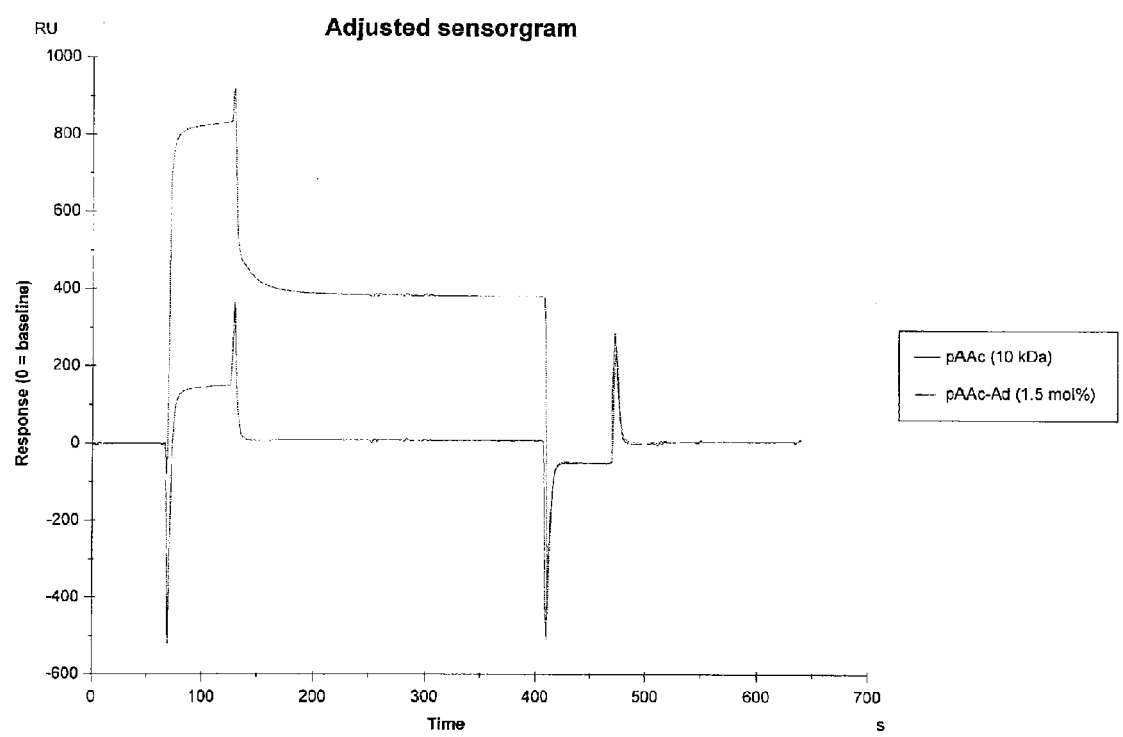
FIG. 14 is a reference-subtracted sensorgram for the interaction of a 1 mM aqueous pAAc control solution with a CD-modified (245 RUs) sensor chip. The baseline was adjusted to 0 in order to demonstrate the magnitude of the binding response. A indicates injection of pAAc or pAAc-Ad-1.5 solution. B indicates the beginning of the dissociation phase. C indicates injection of a 10 mM aqueous CD solution for regeneration of the sensor chip. D indicates a washing step using 1×PBS.

In order to examine the propensity for nonspecific interactions to occur, a 1 mM aqueous solution of pAAc (no Ad groups) was utilized as a negative control in a binding study. As before, the solution was passed over the CD-containing matrix as well as a carboxymethylated-dextran reference surface, and the response at the reference surface was subtracted from the response at the CD-containing surface to give FIG. 14. There is a positive binding response for pAAc within the CD-containing matrix; however, the signal nearly returns to baseline upon washing with 1×PBS. Thus, it appears that there are some nonspecific interactions between the CD-matrix and unmodified pAAc. Although, the magnitude of the binding response is significantly lower than the response obtained for pAAc-Ad-1.5, indicating that much less pAAc is binding to the CD-matrix.

Figure 15:
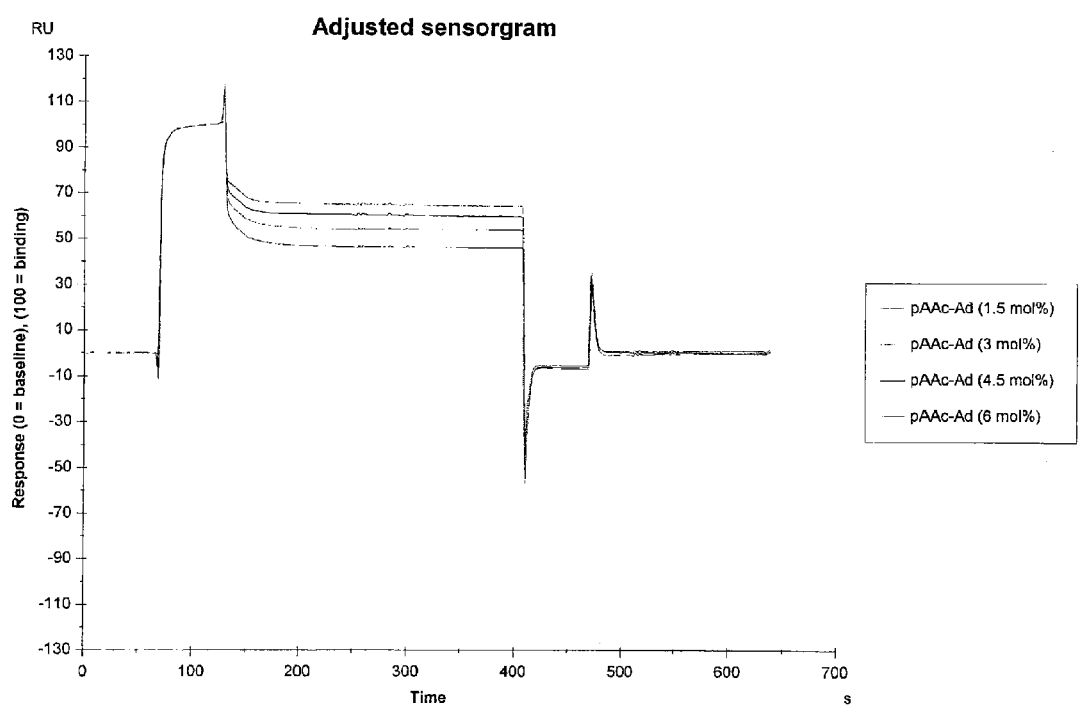
FIG. 15 is a reference-subtracted, normalized sensorgrams for the interaction of the various pAAc-Ad derivatives with a CD-modified (245 RUs) sensor chip. The baseline was adjusted to 0 in order to demonstrate the magnitude of the binding response. The maximum binding response was normalized to 100 RUs to demonstrate the relative stabilities. A indicates injection of the pAAc-Ad derivative. B indicates the beginning of the dissociation phase. C indicates injection of a 10 mM aqueous CD solution for regeneration of the sensor chip. D indicates a washing step using 1×PBS.

Based on the data contained in the preceding sensorgrams, this appears to be a relatively good model for examining multivalent interactions. Thus, this model was used to examine the effects of varying the guest (Ad) density on the stability of the interaction. It has been hypothesized that higher Ad densities will lead to more stable interactions, which should afford the opportunity to fine-tune drug release profiles by simply altering the number of interactions between the drug and the drug delivery platform. Reference-subtracted sensorgrams were obtained for each of the pAAc-Ad derivatives as before. All of the sensorgrams were then normalized to give a maximum binding response of 100 RUs, and were then superimposed on the same plot (FIG. 15) in order to demonstrate the effect of increasing Ad density on interaction stability.

Figure 16:
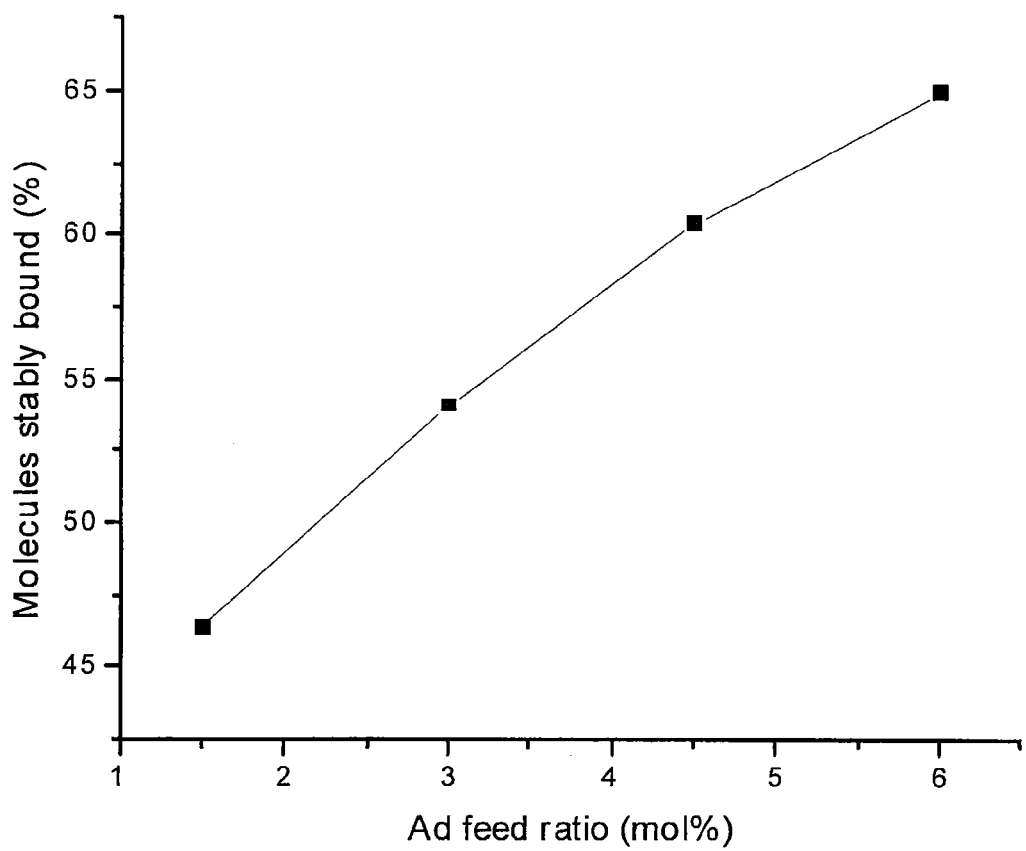
FIG. 16 is a plot showing the relationship between Ad density and the stability of the multivalent interaction.

As was expected, the stability of the interaction increased (nearly linearly; see FIG. 16) with increasing Ad density. This indicates that not only can the Ad density be fine-tuned to adjust the kinetics of the interaction, but such a system could be used to release multiple therapeutic agents at different rates. Interestingly, even at relatively high Ad densities (theoretically up to 8 Ad groups per polymer chain), the interactions were reversible upon addition of a monovalent competitor (CD). Stability constants for the monovalent interaction of Ad with CD in solution have been reported to be on the order of $5 \times 10^4$ M$^{-1}$. For a $C_{eff,max}$ of approximately 2.1 mM and up to 8 interactions, equation 1 can be used to estimate the overall stability constant to be approximately $7 \times 10^{18}$ M$^{-1}$. This is starting to borderline on irreversible interactions such as the streptavidin-biotin interaction. However, the complete dissociation can once again be attributed to the relatively low $C_{eff,max}$ value. Due to the fact that the concentration of free monovalent competitor in solution is approximately 5-fold higher than the effective concentration in the matrix, intermolecular binding will be favored over intramolecular binding leading to dissociation. The effect of monovalent competitors must be taken into account when designing a drug delivery device that is to be implanted, as there exist a number of molecules within the body (e.g., cholesterol) that can compete for CD binding sites.

Example 6 CD-Hydrogels

Preparation of CD Hydrogels

In order to make the β-cyclodextrin-Epichlorohydrin copolymer insoluble for applications as a drug delivery platform, a hydrogel was formed via crosslinking using a triisocyanate. Briefly, 1.0 g (0.84 mmol of CD repeats) of β-cyclodextrin-Epichlorohydrin copolymer was dissolved in 10 ml of DMF at room temperature under constant stirring. The solution was contained in a cylindrical glass mold with an O.D. of 6 cm. Once all of the copolymer had dissolved, 1.139 ml of Desmodur RE (0.84 mmol of triphenylmethane-4,4',4"-triisocyanate) was added under constant stirring and allowed to mix until the solution had turned a dark violet color. The solution was then heated to 60° C. until gellation occurred. The gel was allowed to cool to room temperature, at which point cylindrical plugs were cut from the gel using a 5 mm stainless steel core punch. The plugs were then incubated in 5 L of Millipore water under constant stirring for 24 hours in order to exchange solvents and remove unreacted reagents.

Following incubation of the plugs in Millipore water for an extended period of time (a minimum of 24 hours) the equilibrium swelling ratio was determined A total of eight plugs were used in the calculation. Each plug was gently dabbed with a kimwipe in order to remove excess water and the mass of the wet gel ($M_w$) was measured. The fact that the plugs had reached equilibrium was verified by measuring the plugs at different time points until no changes were detected in the measured mass. Once the mass of the wet gel was obtained the plugs were dried in an oven at 50° C., again until no change in the measured mass was detected, at which time the mass of the dry gel ($M_d$) was measured. The swelling ratio was then calculated using equation 2:

$$\text{Swelling ratio} = \frac{M_w}{M_d} \quad (2)$$

In Vitro Drug Loading 0.4 mM stock solutions of LRB-pAAc, LRB-pAAc-Ad-1.5, and LRB-pAAc-Ad-6 were prepared in Millipore water. From these stock solutions, dilutions of 1:2 (0.2 mM solution) and 1:4 (0.1 mM solution) were prepared for each sample. A cylindrical hydrogel plug, which had been incubated in Millipore water for a minimum of 24 hours, was gently dabbed using a kimwipe to remove excess water and then weighed in order to determine the mass of the wet gel. The plug was then incubated in 280 μL of the desired solution. A total of three (n=3) plugs were used at each concentration for the various samples. 10 μL aliquots were taken from each well at predetermined time points and the water was evaporated in an oven at 50° C. The aliquots were then resuspended in 100 μL of Millipore water, giving a 1:10 dilution of the original aliquot. Solutions containing known concentrations of the various samples were added to the 96 well plates in order to determine a calibration curve. The plates were then analyzed using a Tecan Safire plate reader in fluorescence mode, with an excitation wavelength of 560 nm and an emission wavelength of 581 nm. Using the obtained calibration curves the measured relative fluorescence units (RFUs) were converted to concentrations and the cumulative loading of each sample was determined. In order to remove variation due to nonuniformities between the various plugs, the loading was normalized to the mass of the gel.

Results
SPR Analysis
Preparation of CD Hydrogels

In order to examine the efficacy of employing multivalent interactions as a means of fine-tuning drug loading and release profiles a hydrogel was prepared using a CD-Epichlorohydrin copolymer. Based on the amount of copolymer used and the total volume of the gel, the average concentration, $C_{avg}$, of CD in the gel was estimated to be approximately 75 mM. Thus, for sufficiently long linker lengths the $C_{eff,max}$ of the gel will approach 75 mM, which is significantly higher (~35-fold) than the value obtained for the sensor chip used in the SPR experiments. Theoretically, much higher concentrations of monovalent competitor would now be required to cause complete dissociation. Additionally, the swelling ratio of the gel was calculated according to equation 2 using a total of 8 cylindrical plugs to be 7.9±0.3. This is an important parameter as the gel must have sufficiently large pores to allow for the pAAc-Ad derivatives to diffuse.

In Vitro Drug Loading

Figure 17:
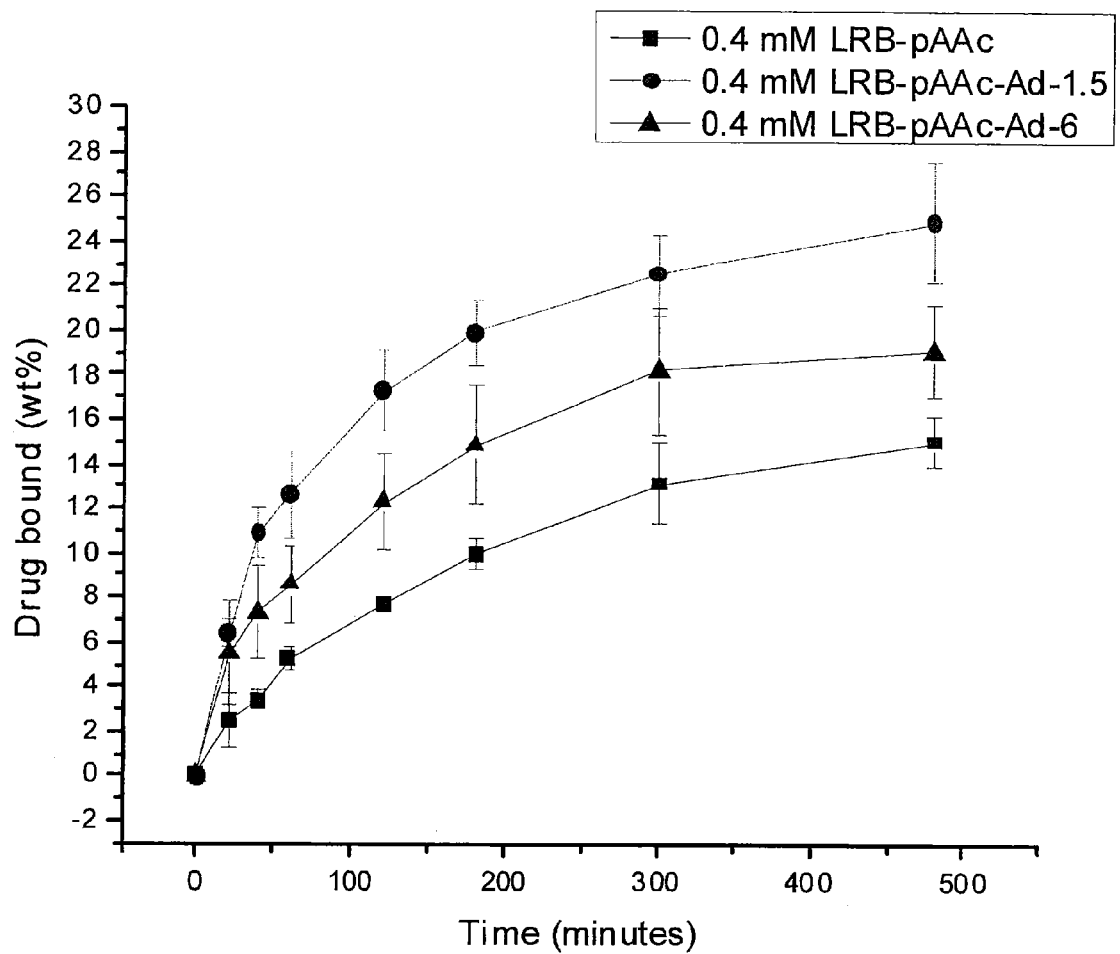
FIG. 17 is a plot showing drug loading profiles for various model drugs (differing in the number of Adamantane arms) at a concentration of 0.4 mM. Data points represent the mean value, while error bars represent the standard deviation (n=3)

Hydrogel plugs were loaded with LRB-pAAc, LRB-pAAc-Ad-1.5, and LRB-pAAc-Ad-6 at varying concentrations (0.4, 0.2, and 0.1 mM) over a period of eight hours. The uptake of each model drug was monitored throughout this time period to give loading profiles as functions of both time and concentration. Both of these parameters are very important when designing a device that is to be reloaded in situ. The local concentration of the drug may be low, which may be further compounded by rapid clearance of the drug. Thus, a system that is capable of rapidly and selectively taking up the drug from the local environment is highly desirable. As would be expected, both the rate and total amount of model drug taken up by the hydrogel plugs increased with increasing concentrations for each system (data not shown). More interesting was the examination of the drug loading profiles of the various model drugs at a given concentration (FIG. 17).

As would be expected, the Ad-modified pAAc molecules were taken up more rapidly and to a greater extent than the unmodified negative control (pAAc) by the hydrogel plugs. This is due to the ability of the Ad-modified pAAc molecules to form selective interactions with the copolymer matrix. Interestingly, the hydrogel plugs were apparently most selective for the LRB-pAAc-Ad-1.5 model as compared to the model containing the higher Ad density (LRB-pAAc-Ad-6). This might be attributable to the higher binding stability of the LRB-pAAc-Ad-6 system. Such a high binding stability might have impeded diffusion of molecules into the gel. The lower binding stability of the LRB-pAAc-Ad-1.5 system might have afforded the opportunity to form selective interactions with more flexibility, allowing molecules to penetrate more deeply. As discussed previously, the drug delivery device should be able to selectively take up drug rapidly from the local environment. The role of multivalent interactions in increasing loading rates is readily apparent when comparing the loading profiles for the LRB-pAAc-Ad-1.5 and LRB-pAAc systems. After only one hour, nearly as much LRB-pAAc-Ad-1.5 had been taken up by the hydrogels as LRB-pAAc loaded over the entire eight hour period.

From the above description of the invention, those skilled in the art will perceive improvements, changes and modifications. Such improvements, changes, and modifications are within the skill of the art and are intended to be covered by the appended claims.

Having described the invention, the following is claimed:

1. A composition formulated for administration to a subject, the composition comprising:
   1) a water-insoluble therapeutic guest agent delivery system, comprising:
      a) a polymer substrate comprising a non-cyclodextrin biocompatible polymer; and
      b) a host comprising a cyclodextrin that is coupled to the polymer substrate, the host having a structure that defines a plurality of pockets for releasably binding a therapeutic guest agent, so that the therapeutic guest agent is released from the delivery system over time after being administered to a subject, wherein the polymer substrate is substituted with at least 10% host molecule; and
   2) a therapeutic guest agent bound to the host of 1b;
   wherein the composition is formulated to remain implanted in a desired area and not migrate as a result of fluid flow through the area.

2. The composition of claim 1, wherein the host is covalently associated with the substrate.

3. The composition of claim 2, wherein the substrate is or comprises a crosslinked cyclodextrin.

4. The composition of claim 3, wherein the substrate and the host comprise the same type of crosslinked cyclodextrin.

5. The composition of claim 1, wherein the crosslinked cyclodextrin comprises β-cyclodextrin-epichlorohydrin copolymer.

6. The composition of claim 5, wherein the β-cyclodextrin-epichlorohydrin copolymer is crosslinked with a trifunctional crosslinker.

7. The composition of claim 5, wherein the β-cyclodextrin-epichlorohydrin copolymer is crosslinked with triphenylmethane-4,4'4"-triisocyanate or lysine triisocyanate.

8. The composition of claim 7, wherein the β-cyclodextrin-epichlorohydrin copolymer is crosslinked with triphenylmethane-4,4',4"-triisocyanate or lysine triisocyanate.

9. The composition of claim 1, wherein the crosslinked cyclodextrin comprises at least one of α-cyclodextrin, β-cyclodextrin or γ-cyclodextrin.

10. The composition of claim 1, further comprising a second therapeutic reagent.

11. The composition of claim 1, further comprising at least one tuning molecule.

12. The composition of claim 1, wherein the composition is capable of being injected to a desired area.

13. The composition of claim 1, wherein the delivery system is a gel.

14. The composition of claim 1, wherein the polymer substrate comprises a polymer selected from the group consisting of polyalkylene oxide, polymethacrylate, polyurethane, cellulosic, polyhydroxyalkyl acrylate, and polyester.

15. The composition of claim 1, wherein the polymer substrate comprises a polyethylene or polyamide selected from the group consisting of polyethylene glycol, polyethylene oxide, polyethyleneimine, poly(L-lactide), poly-p-dioxanone, polycaprolactone, polyvinyl alcohol, and poly(lactide-co-glycolide).

16. The composition of claim 1, wherein the composition comprises a crosslinked polymer disk.

17. An implantable device coated with the composition of claim 1.

18. The implantable device of claim 17, wherein the device is an orthopedic implant.

* * * * *